(12) United States Patent
Panken

(10) Patent No.: US 9,327,129 B2
(45) Date of Patent: May 3, 2016

(54) BLENDED POSTURE STATE CLASSIFICATION AND THERAPY DELIVERY

(75) Inventor: Eric J. Panken, Edina, MN (US)

(73) Assignee: Medtronic, Inc., Minneapolis, MN (US)

( * ) Notice: Subject to any disclaimer, the term of this patent is extended or adjusted under 35 U.S.C. 154(b) by 2059 days.

(21) Appl. No.: 12/433,038

(22) Filed: Apr. 30, 2009

(65) Prior Publication Data

US 2010/0010382 A1    Jan. 14, 2010

Related U.S. Application Data

(60) Provisional application No. 61/080,049, filed on Jul. 11, 2008.

(51) Int. Cl.
*A61N 1/00* (2006.01)
*A61N 1/365* (2006.01)
*A61B 5/11* (2006.01)
*A61B 5/00* (2006.01)

(52) U.S. Cl.
CPC .......... *A61N 1/36542* (2013.01); *A61B 5/1116* (2013.01); *A61B 5/7264* (2013.01); *A61B 5/1118* (2013.01); *A61B 5/686* (2013.01); *A61B 2562/0219* (2013.01); *A61N 1/36535* (2013.01)

(58) Field of Classification Search
CPC ............................ A61N 1/3542; A61B 5/1116
USPC .......................................... 607/17–19, 62, 64
See application file for complete search history.

(56) References Cited

U.S. PATENT DOCUMENTS

| 4,297,685 A | 10/1981 | Brainard, II |
| 4,365,633 A | 12/1982 | Loughman |
| 4,543,955 A | 10/1985 | Schroeppel |

(Continued)

FOREIGN PATENT DOCUMENTS

| DE | 19831109 | 1/2000 |
| DE | 10024103 | 11/2001 |

(Continued)

OTHER PUBLICATIONS

"Analysis of heart rate dynamics by methods derived from non-linear mathematics: Clinical applicability and prognostic significance," http://herkules.oulu.fi.isbn9514250133/html, 4 pp., 2004.

(Continued)

*Primary Examiner* — Theodore Stigell
*Assistant Examiner* — Nadia A Mahmood
(74) *Attorney, Agent, or Firm* — Beth L. McMahon

(57) ABSTRACT

Techniques for classification of a posture state of a patient using multiple posture state definitions, and for delivering therapy according to the patient's classified posture state. Detected parameter values describing a patient's posture state are compared to posture state definitions. This comparison is used to determine similarity values describing how similar the patient's posture state is to each of the posture states described by the posture state definitions. Weighting factors may be determined from the similarity values and used to weight therapy parameter values that are associated with each of the posture state definitions. The resulting weighted therapy parameter values may be used to derive a blended therapy parameter value for use in delivering therapy to the patient. The patient's posture state may be expressed in terms of a blending of the multiple posture state definitions.

32 Claims, 14 Drawing Sheets

(56) References Cited

U.S. PATENT DOCUMENTS

| | | |
|---|---|---|
| 4,550,736 A | 11/1985 | Broughton et al. |
| 4,566,456 A | 1/1986 | Koning et al. |
| 4,771,780 A | 9/1988 | Sholder |
| 4,776,345 A | 10/1988 | Cohen et al. |
| 4,846,180 A | 7/1989 | Buffet |
| 4,846,195 A | 7/1989 | Alt |
| 5,031,618 A | 7/1991 | Mullett |
| 5,040,534 A | 8/1991 | Mann et al. |
| 5,040,536 A | 8/1991 | Riff |
| 5,058,584 A | 10/1991 | Bourgeois |
| 5,125,412 A | 6/1992 | Thornton |
| 5,154,180 A | 10/1992 | Blanchet et al. |
| 5,158,078 A | 10/1992 | Bennett et al. |
| 5,167,229 A | 12/1992 | Peckham et al. |
| 5,233,984 A | 8/1993 | Thompson |
| 5,275,159 A | 1/1994 | Griebel |
| 5,312,446 A | 5/1994 | Holschbach et al. |
| 5,335,657 A | 8/1994 | Terry, Jr. et al. |
| 5,337,758 A | 8/1994 | Moore et al. |
| 5,342,409 A | 8/1994 | Mullett |
| 5,354,317 A | 10/1994 | Alt |
| 5,425,750 A | 6/1995 | Moberg |
| 5,476,483 A | 12/1995 | Bornzin et al. |
| 5,487,755 A | 1/1996 | Snell et al. |
| 5,513,645 A | 5/1996 | Jacobson et al. |
| 5,514,162 A | 5/1996 | Bornzin et al. |
| 5,558,640 A | 9/1996 | Pfeiler et al. |
| 5,562,707 A | 10/1996 | Prochazka et al. |
| 5,593,431 A | 1/1997 | Sheldon |
| 5,622,428 A | 4/1997 | Bonnet |
| 5,628,317 A | 5/1997 | Starkebaum et al. |
| 5,643,332 A | 7/1997 | Stein |
| 5,645,053 A | 7/1997 | Remmers et al. |
| 5,674,258 A | 10/1997 | Henschel et al. |
| 5,711,316 A | 1/1998 | Elsberry et al. |
| 5,720,770 A | 2/1998 | Nappholz et al. |
| 5,732,696 A | 3/1998 | Rapoport et al. |
| 5,741,310 A | 4/1998 | Wittkampf |
| 5,782,884 A | 7/1998 | Stotts et al. |
| 5,814,093 A | 9/1998 | Stein |
| 5,832,932 A | 11/1998 | Elsberry et al. |
| 5,833,709 A | 11/1998 | Rise et al. |
| 5,836,989 A | 11/1998 | Shelton |
| 5,851,193 A | 12/1998 | Arikka et al. |
| 5,865,760 A | 2/1999 | Lidman et al. |
| 5,885,471 A | 3/1999 | Ruben et al. |
| 5,893,883 A | 4/1999 | Torgerson et al. |
| 5,895,371 A | 4/1999 | Levitas et al. |
| 5,904,708 A | 5/1999 | Goedeke |
| 5,911,738 A | 6/1999 | Sikorski et al. |
| 5,913,727 A | 6/1999 | Ahdoot |
| 5,919,149 A | 7/1999 | Allum |
| 5,938,690 A | 8/1999 | Law et al. |
| 5,941,906 A | 8/1999 | Barreras, Sr. et al. |
| 5,944,680 A | 8/1999 | Christopherson et al. |
| 5,957,957 A | 9/1999 | Sheldon |
| 6,027,456 A | 2/2000 | Feler et al. |
| 6,038,475 A | 3/2000 | Sikorski et al. |
| 6,044,297 A | 3/2000 | Sheldon et al. |
| 6,045,513 A | 4/2000 | Stone et al. |
| 6,059,576 A | 5/2000 | Brann |
| 6,095,991 A | 8/2000 | Krausman et al. |
| 6,099,479 A | 8/2000 | Christopherson et al. |
| 6,102,874 A | 8/2000 | Stone et al. |
| 6,120,467 A | 9/2000 | Schallhorn |
| 6,128,534 A | 10/2000 | Park et al. |
| 6,134,459 A | 10/2000 | Roberts et al. |
| 6,157,857 A | 12/2000 | Dimpfel |
| 6,165,143 A | 12/2000 | Van Lummel |
| 6,216,537 B1 | 4/2001 | Henschel et al. |
| 6,259,948 B1 | 7/2001 | Florio et al. |
| 6,280,409 B1 | 8/2001 | Stone et al. |
| 6,296,606 B1 | 10/2001 | Goldberg et al. |
| 6,308,098 B1 | 10/2001 | Meyer |
| 6,308,099 B1 | 10/2001 | Fox et al. |
| 6,315,740 B1 | 11/2001 | Singh |
| 6,327,501 B1 | 12/2001 | Levine et al. |
| 6,341,236 B1 | 1/2002 | Osorio et al. |
| 6,351,672 B1 | 2/2002 | Park et al. |
| 6,368,284 B1 | 4/2002 | Bardy |
| 6,381,496 B1 | 4/2002 | Meadows et al. |
| 6,393,325 B1 | 5/2002 | Mann et al. |
| 6,438,408 B1 | 8/2002 | Mulligan et al. |
| 6,440,090 B1 | 8/2002 | Schallhorn |
| 6,449,508 B1 | 9/2002 | Sheldon et al. |
| 6,459,934 B1 | 10/2002 | Kadhiresan |
| 6,466,821 B1 | 10/2002 | Pianca et al. |
| 6,468,234 B1 | 10/2002 | Van der Loos et al. |
| 6,507,757 B1 | 1/2003 | Swain et al. |
| 6,514,218 B2 | 2/2003 | Yamamoto |
| 6,516,749 B1 | 2/2003 | Salasidis |
| 6,539,249 B1 | 3/2003 | Kadhiresan et al. |
| 6,547,755 B1 | 4/2003 | Lippe et al. |
| 6,572,557 B2 | 6/2003 | Tchou et al. |
| 6,574,507 B1 | 6/2003 | Bonnet |
| 6,605,038 B1 | 8/2003 | Teller et al. |
| 6,609,031 B1 | 8/2003 | Law et al. |
| 6,611,783 B2 | 8/2003 | Kelly, Jr. et al. |
| 6,620,151 B2 | 9/2003 | Blischak et al. |
| 6,625,493 B2 | 9/2003 | Kroll et al. |
| 6,635,048 B1 | 10/2003 | Ullestad et al. |
| 6,641,542 B2 | 11/2003 | Cho et al. |
| 6,658,292 B2 | 12/2003 | Kroll et al. |
| 6,659,968 B1 | 12/2003 | McClure |
| 6,662,047 B2 | 12/2003 | Sorensen |
| 6,665,558 B2 | 12/2003 | Kalgren et al. |
| 6,668,188 B2 | 12/2003 | Sun et al. |
| 6,687,538 B1 | 2/2004 | Hrdlicka et al. |
| 6,731,984 B2 | 5/2004 | Cho et al. |
| 6,740,075 B2 | 5/2004 | Lebel et al. |
| 6,748,276 B1 | 6/2004 | Daignault, Jr. et al. |
| 6,752,766 B2 | 6/2004 | Kowallik et al. |
| 6,773,404 B2 | 8/2004 | Poezevera et al. |
| 6,782,315 B2 | 8/2004 | Lu et al. |
| 6,817,979 B2 | 11/2004 | Nihtilä |
| 6,820,025 B2 | 11/2004 | Bachmann et al. |
| 6,829,507 B1 | 12/2004 | Lidman et al. |
| 6,832,113 B2 | 12/2004 | Belalcazar |
| 6,834,436 B2 | 12/2004 | Townsend et al. |
| 6,853,863 B2 | 2/2005 | Carter et al. |
| 6,878,121 B2 | 4/2005 | Krausman et al. |
| 6,879,352 B1 | 4/2005 | Kim |
| 6,884,596 B2 | 4/2005 | Civelli et al. |
| 6,890,306 B2 | 5/2005 | Poezevera |
| 6,895,341 B2 | 5/2005 | Barrey et al. |
| 6,922,587 B2 | 7/2005 | Weinberg |
| 6,923,784 B2 | 8/2005 | Stein |
| 6,928,324 B2 | 8/2005 | Park et al. |
| 6,937,899 B2 | 8/2005 | Sheldon et al. |
| 6,937,900 B1 | 8/2005 | Pianca et al. |
| 6,945,934 B2 | 9/2005 | Bardy |
| 6,964,641 B2 | 11/2005 | Cho et al. |
| 6,975,904 B1 | 12/2005 | Sloman |
| 6,997,882 B1 | 2/2006 | Parker et al. |
| 6,999,817 B2 | 2/2006 | Park et al. |
| 7,016,730 B2 | 3/2006 | Ternes |
| 7,031,772 B2 | 4/2006 | Condie |
| 7,043,305 B2 | 5/2006 | KenKnight et al. |
| 7,054,687 B1 | 5/2006 | Andersen |
| 7,066,910 B2 | 6/2006 | Bauhahn et al. |
| 7,082,333 B1 | 7/2006 | Bauhahn |
| 7,092,759 B2 | 8/2006 | Nehls et al. |
| 7,095,424 B2 | 8/2006 | Satoh et al. |
| 7,110,820 B2 | 9/2006 | Tcheng et al. |
| 7,117,036 B2 | 10/2006 | Florio |
| 7,123,967 B2 | 10/2006 | Weinberg |
| 7,130,681 B2 | 10/2006 | Gebhardt et al. |
| 7,130,689 B1 | 10/2006 | Turcott |
| 7,141,026 B2 | 11/2006 | Aminian et al. |
| 7,142,921 B2 | 11/2006 | Mattes et al. |
| 7,149,579 B1 | 12/2006 | Koh et al. |
| 7,149,584 B1 | 12/2006 | Koh et al. |
| 7,151,961 B1 | 12/2006 | Whitehurst et al. |
| 7,155,279 B2 | 12/2006 | Whitehurst et al. |

(56) References Cited

U.S. PATENT DOCUMENTS

| | | |
|---|---|---|
| 7,160,252 B2 | 1/2007 | Cho et al. |
| 7,162,304 B1 | 1/2007 | Bradley |
| 7,167,743 B2 | 1/2007 | Heruth et al. |
| 7,167,751 B1 | 1/2007 | Whitehurst et al. |
| 7,181,281 B1 | 2/2007 | Kroll |
| 7,189,204 B2 | 3/2007 | Ni et al. |
| 7,207,947 B2 | 4/2007 | Koh et al. |
| 7,210,240 B2 | 5/2007 | Townsend et al. |
| 7,212,862 B2 | 5/2007 | Park et al |
| 7,214,197 B2 | 5/2007 | Prass |
| 7,218,964 B2 | 5/2007 | Hill et al. |
| 7,218,968 B2 | 5/2007 | Condie et al. |
| 7,221,979 B2 | 5/2007 | Zhou et al. |
| 7,231,254 B2 | 6/2007 | DiLorenzo |
| 7,242,983 B2 | 7/2007 | Frei et al. |
| 7,252,640 B2 | 8/2007 | Ni et al. |
| 7,266,412 B2 | 9/2007 | Stypulkowski |
| 7,308,311 B2 | 12/2007 | Sorensen et al. |
| 7,313,440 B2 | 12/2007 | Miesel |
| 7,317,948 B1 | 1/2008 | King et al. |
| 7,330,760 B2 | 2/2008 | Heruth et al. |
| 7,366,569 B2 | 4/2008 | Belalcazar |
| 7,366,572 B2 | 4/2008 | Heruth et al. |
| 7,387,610 B2 | 6/2008 | Stahmann |
| 7,389,147 B2 | 6/2008 | Wahlstrand et al. |
| 7,395,113 B2 | 7/2008 | Heruth |
| 7,403,820 B2 | 7/2008 | DiLorenzo |
| 7,406,351 B2 | 7/2008 | Wesselink |
| 7,415,308 B2 | 8/2008 | Gerber et al. |
| 7,447,545 B2 | 11/2008 | Heruth et al. |
| 7,471,290 B2 | 12/2008 | Wang et al. |
| 7,471,980 B2 | 12/2008 | Koshiol |
| 7,489,970 B2 | 2/2009 | Lee et al. |
| 7,491,181 B2 | 2/2009 | Heruth et al. |
| 7,505,815 B2 | 3/2009 | Lee et al. |
| 7,519,431 B2 | 4/2009 | Goetz et al. |
| 7,542,803 B2 | 6/2009 | Heruth et al. |
| 7,548,786 B2 | 6/2009 | Lee et al. |
| 7,559,901 B2 | 7/2009 | Maile |
| 7,572,225 B2 | 8/2009 | Stahmann |
| 7,577,479 B2 | 8/2009 | Hartley et al. |
| 7,580,752 B2 | 8/2009 | Gerber et al. |
| 7,584,808 B2 | 9/2009 | Dolgin et al. |
| 7,590,453 B2 | 9/2009 | Heruth |
| 7,590,455 B2 | 9/2009 | Heruth et al. |
| 7,590,481 B2 | 9/2009 | Lu et al. |
| 7,591,265 B2 | 9/2009 | Lee et al. |
| 7,603,170 B2 | 10/2009 | Hatlestad et al. |
| 7,623,919 B2 | 11/2009 | Goetz et al. |
| 7,634,379 B2 | 12/2009 | Noble |
| 7,664,546 B2 | 2/2010 | Hartley et al. |
| 7,672,806 B2 | 3/2010 | Tronconi |
| 7,717,848 B2 | 5/2010 | Heruth et al. |
| 7,769,464 B2 | 8/2010 | Gerber et al. |
| 7,792,583 B2 | 9/2010 | Heruth et al. |
| 7,826,981 B2 | 11/2010 | Goode et al. |
| 8,529,448 B2 | 9/2013 | McNair |
| 8,649,862 B2 | 2/2014 | Ludwig et al. |
| 2002/0038137 A1 | 3/2002 | Stein |
| 2002/0091308 A1 | 7/2002 | Kipshidze et al. |
| 2002/0107553 A1 | 8/2002 | Hill et al. |
| 2002/0115939 A1 | 8/2002 | Mulligan et al. |
| 2002/0165586 A1 | 11/2002 | Hill et al. |
| 2002/0169485 A1 | 11/2002 | Pless et al. |
| 2002/0170193 A1 | 11/2002 | Townsend et al. |
| 2003/0004423 A1 | 1/2003 | Lavie et al. |
| 2003/0036783 A1 | 2/2003 | Bauhahn et al. |
| 2003/0045910 A1 | 3/2003 | Sorensen et al. |
| 2003/0065370 A1 | 4/2003 | Lebel et al. |
| 2003/0088185 A1 | 5/2003 | Prass |
| 2003/0149457 A1 | 8/2003 | Tcheng et al. |
| 2003/0171791 A1 | 9/2003 | KenKnight et al. |
| 2003/0181960 A1 | 9/2003 | Carter et al. |
| 2003/0204211 A1 | 10/2003 | Condie et al. |
| 2004/0015103 A1* | 1/2004 | Aminian et al. ............. 600/595 |
| 2004/0049132 A1 | 3/2004 | Barron et al. |
| 2004/0088020 A1 | 5/2004 | Condie et al. |
| 2004/0102814 A1 | 5/2004 | Sorensen et al. |
| 2004/0133248 A1 | 7/2004 | Frei et al. |
| 2004/0138716 A1 | 7/2004 | Kon et al. |
| 2004/0147975 A1 | 7/2004 | Popovic et al. |
| 2004/0199215 A1 | 10/2004 | Lee et al. |
| 2004/0199216 A1 | 10/2004 | Lee et al. |
| 2004/0199217 A1 | 10/2004 | Lee et al. |
| 2004/0199218 A1 | 10/2004 | Lee et al. |
| 2004/0215286 A1 | 10/2004 | Stypulkowski |
| 2004/0220621 A1 | 11/2004 | Zhou et al. |
| 2004/0225332 A1 | 11/2004 | Gebhardt et al. |
| 2004/0257693 A1 | 12/2004 | Ehrlich |
| 2005/0042589 A1 | 2/2005 | Hatlestad et al. |
| 2005/0043767 A1 | 2/2005 | Belalcazar |
| 2005/0060001 A1 | 3/2005 | Singhal et al. |
| 2005/0061320 A1 | 3/2005 | Lee et al. |
| 2005/0113710 A1 | 5/2005 | Stahmann et al. |
| 2005/0113887 A1 | 5/2005 | Bauhahn |
| 2005/0126026 A1 | 6/2005 | Townsend et al. |
| 2005/0137627 A1 | 6/2005 | Koshiol et al. |
| 2005/0145246 A1 | 7/2005 | Hartley et al. |
| 2005/0172311 A1 | 8/2005 | Hjelt et al. |
| 2005/0177192 A1 | 8/2005 | Rezai et al. |
| 2005/0209511 A1 | 9/2005 | Heruth et al. |
| 2005/0209512 A1 | 9/2005 | Heruth et al. |
| 2005/0209513 A1 | 9/2005 | Heruth et al. |
| 2005/0209643 A1 | 9/2005 | Heruth et al. |
| 2005/0209644 A1 | 9/2005 | Heruth et al. |
| 2005/0209645 A1* | 9/2005 | Heruth et al. ............. 607/3 |
| 2005/0215847 A1 | 9/2005 | Heruth et al. |
| 2005/0215947 A1 | 9/2005 | Heruth et al. |
| 2005/0216064 A1 | 9/2005 | Heruth et al. |
| 2005/0222522 A1 | 10/2005 | Heruth et al. |
| 2005/0222638 A1 | 10/2005 | Foley et al. |
| 2005/0228455 A1 | 10/2005 | Kramer et al. |
| 2005/0234514 A1 | 10/2005 | Heruth et al. |
| 2005/0234518 A1 | 10/2005 | Heruth et al. |
| 2005/0240242 A1 | 10/2005 | DiLorenzo |
| 2005/0245988 A1 | 11/2005 | Miesel |
| 2005/0283210 A1 | 12/2005 | Blischak et al. |
| 2006/0190049 A1 | 8/2006 | Gerber et al. |
| 2006/0190050 A1 | 8/2006 | Gerber et al. |
| 2006/0190051 A1 | 8/2006 | Gerber et al. |
| 2006/0195051 A1 | 8/2006 | Schnapp et al. |
| 2006/0206167 A1 | 9/2006 | Flaherty et al. |
| 2006/0212080 A1 | 9/2006 | Hartley et al. |
| 2006/0213267 A1 | 9/2006 | Tronconi et al. |
| 2006/0235289 A1 | 10/2006 | Wesselink et al. |
| 2006/0235472 A1 | 10/2006 | Goetz et al. |
| 2006/0241513 A1 | 10/2006 | Hatlestad et al. |
| 2006/0247732 A1 | 11/2006 | Wesselink |
| 2006/0247739 A1 | 11/2006 | Wahlstrand et al. |
| 2006/0253043 A1 | 11/2006 | Zhang et al. |
| 2006/0259099 A1 | 11/2006 | Goetz et al. |
| 2006/0262120 A1 | 11/2006 | Rosenberg |
| 2006/0265025 A1 | 11/2006 | Goetz et al. |
| 2006/0284979 A1 | 12/2006 | Clarkson |
| 2006/0287686 A1 | 12/2006 | Cullen et al. |
| 2007/0015976 A1 | 1/2007 | Miesel et al. |
| 2007/0032748 A1 | 2/2007 | McNeil et al. |
| 2007/0038265 A1 | 2/2007 | Tcheng et al. |
| 2007/0050715 A1 | 3/2007 | Behar |
| 2007/0073355 A1 | 3/2007 | DiLorenzo et al. |
| 2007/0115277 A1 | 5/2007 | Wang et al. |
| 2007/0118056 A1 | 5/2007 | Wang et al. |
| 2007/0123758 A1 | 5/2007 | Miesel et al. |
| 2007/0129622 A1 | 6/2007 | Bourget et al. |
| 2007/0129641 A1 | 6/2007 | Sweeney |
| 2007/0129769 A1 | 6/2007 | Bourget et al. |
| 2007/0129774 A1 | 6/2007 | Bourget et al. |
| 2007/0150026 A1 | 6/2007 | Bourget et al. |
| 2007/0150029 A1 | 6/2007 | Bourget et al. |
| 2007/0213789 A1 | 9/2007 | Nolan et al. |
| 2007/0249968 A1 | 10/2007 | Miesel et al. |
| 2007/0250121 A1 | 10/2007 | Miesel et al. |
| 2007/0250134 A1 | 10/2007 | Miesel et al. |
| 2007/0255118 A1 | 11/2007 | Miesel et al. |

(56) References Cited

U.S. PATENT DOCUMENTS

| | | |
|---|---|---|
| 2007/0255154 A1 | 11/2007 | Lu et al. |
| 2007/0265664 A1 | 11/2007 | Gerber et al. |
| 2007/0265681 A1 | 11/2007 | Gerber et al. |
| 2007/0276439 A1 | 11/2007 | Miesel et al. |
| 2007/0293737 A1 | 12/2007 | Heruth et al. |
| 2007/0293917 A1 | 12/2007 | Thompson |
| 2008/0071150 A1 | 3/2008 | Miesel et al. |
| 2008/0071324 A1 | 3/2008 | Miesel et al. |
| 2008/0071326 A1 | 3/2008 | Heruth et al. |
| 2008/0071327 A1 | 3/2008 | Miesel et al. |
| 2008/0079444 A1 | 4/2008 | Denison |
| 2008/0081958 A1 | 4/2008 | Denison et al. |
| 2008/0114219 A1 | 5/2008 | Zhang et al. |
| 2008/0164979 A1 | 7/2008 | Otto |
| 2008/0177355 A1 | 7/2008 | Miesel et al. |
| 2008/0188901 A1 | 8/2008 | Sanghera et al. |
| 2008/0188909 A1 | 8/2008 | Bradley |
| 2008/0194998 A1 | 8/2008 | Holmstrom et al. |
| 2008/0204255 A1 | 8/2008 | Flexer et al. |
| 2008/0269812 A1 | 10/2008 | Gerber et al. |
| 2008/0269843 A1 | 10/2008 | Gerber |
| 2008/0281376 A1 | 11/2008 | Gerber et al. |
| 2008/0281379 A1 | 11/2008 | Wesselink |
| 2008/0281381 A1 | 11/2008 | Gerber et al. |
| 2008/0288200 A1 | 11/2008 | Noble |
| 2008/0300449 A1 | 12/2008 | Gerber et al. |
| 2008/0300470 A1 | 12/2008 | Gerber et al. |
| 2009/0030263 A1 | 1/2009 | Heruth et al. |
| 2009/0036951 A1 | 2/2009 | Heruth et al. |
| 2009/0046056 A1 | 2/2009 | Rosenberg et al. |
| 2009/0076343 A1 | 3/2009 | James et al. |
| 2009/0082829 A1 | 3/2009 | Panken et al. |
| 2009/0099627 A1 | 4/2009 | Molnar et al. |
| 2009/0105785 A1 | 4/2009 | Wei et al. |
| 2009/0118599 A1 | 5/2009 | Heruth et al. |
| 2009/0228841 A1 | 9/2009 | Hildreth |
| 2009/0233770 A1 | 9/2009 | Vincent et al. |
| 2009/0259216 A1 | 10/2009 | Drew et al. |
| 2009/0264789 A1 | 10/2009 | Molnar et al. |
| 2009/0306740 A1 | 12/2009 | Heruth et al. |
| 2010/0010380 A1 | 1/2010 | Panken et al. |
| 2010/0010381 A1 | 1/2010 | Skelton et al. |
| 2010/0010382 A1 | 1/2010 | Panken et al. |
| 2010/0010383 A1 | 1/2010 | Skelton et al. |
| 2010/0010384 A1 | 1/2010 | Panken et al. |
| 2010/0010385 A1 | 1/2010 | Skelton et al. |
| 2010/0010386 A1 | 1/2010 | Skelton et al. |
| 2010/0010387 A1 | 1/2010 | Skelton et al. |
| 2010/0010388 A1 | 1/2010 | Panken et al. |
| 2010/0010389 A1 | 1/2010 | Davis et al. |
| 2010/0010390 A1 | 1/2010 | Skelton et al. |
| 2010/0010391 A1 | 1/2010 | Skelton et al. |
| 2010/0010392 A1 | 1/2010 | Skelton et al. |
| 2010/0010432 A1 | 1/2010 | Skelton et al. |
| 2010/0010571 A1 | 1/2010 | Skelton et al. |
| 2010/0010572 A1 | 1/2010 | Skelton et al. |
| 2010/0010573 A1 | 1/2010 | Skelton et al. |
| 2010/0010574 A1 | 1/2010 | Skelton et al. |
| 2010/0010575 A1 | 1/2010 | Skelton et al. |
| 2010/0010576 A1 | 1/2010 | Skelton et al. |
| 2010/0010577 A1 | 1/2010 | Skelton et al. |
| 2010/0010578 A1 | 1/2010 | Skelton et al. |
| 2010/0010579 A1 | 1/2010 | Skelton et al. |
| 2010/0010580 A1 | 1/2010 | Skelton et al. |
| 2010/0010583 A1 | 1/2010 | Panken et al. |
| 2010/0010584 A1 | 1/2010 | Skelton et al. |
| 2010/0010585 A1 | 1/2010 | Davis et al. |
| 2010/0010586 A1 | 1/2010 | Skelton et al. |
| 2010/0010587 A1 | 1/2010 | Skelton et al. |
| 2010/0010588 A1 | 1/2010 | Skelton et al. |
| 2010/0010589 A1 | 1/2010 | Skelton et al. |
| 2010/0010590 A1 | 1/2010 | Skelton et al. |
| 2010/0030286 A1 | 2/2010 | Goetz et al. |
| 2010/0106210 A1* | 4/2010 | Hedberg et al. .......... 607/17 |
| 2010/0121415 A1 | 5/2010 | Skelton et al. |
| 2010/0174155 A1 | 7/2010 | Heruth et al. |

FOREIGN PATENT DOCUMENTS

| | | |
|---|---|---|
| EP | 0564803 | 10/1993 |
| EP | 0845240 | 6/1998 |
| EP | 0849715 | 6/1998 |
| EP | 1195139 | 4/2002 |
| EP | 1291036 | 3/2003 |
| EP | 1308182 | 5/2003 |
| EP | 1391846 | 2/2004 |
| EP | 1437159 | 7/2004 |
| EP | 1731088 | 12/2006 |
| EP | 1731097 A2 | 12/2006 |
| EP | 1870128 | 12/2007 |
| EP | 1938862 | 7/2008 |
| GB | 2330912 | 5/1999 |
| GB | 2408342 | 5/2005 |
| GB | 2447647 | 9/2008 |
| WO | 94/05371 | 3/1994 |
| WO | 96/29007 | 9/1996 |
| WO | 97/04705 | 2/1997 |
| WO | 97/49455 | 12/1997 |
| WO | 98/00197 | 1/1998 |
| WO | 99/56820 | 11/1999 |
| WO | 01/37930 | 5/2001 |
| WO | 02/28282 | 4/2002 |
| WO | 02/41771 | 5/2002 |
| WO | 02/087433 | 11/2002 |
| WO | 02/096512 | 12/2002 |
| WO | 02/100267 | 12/2002 |
| WO | 03/051356 | 6/2003 |
| WO | 03/065891 | 8/2003 |
| WO | 2005/028029 | 3/2005 |
| WO | 2005/035050 | 4/2005 |
| WO | 2005/079487 | 9/2005 |
| WO | 2005/089646 | 9/2005 |
| WO | 2005/089647 | 9/2005 |
| WO | 2005/089860 | 9/2005 |
| WO | 2005/102499 | 11/2005 |
| WO | 2005/120348 | 12/2005 |
| WO | 2007/009088 | 1/2007 |
| WO | 2007/051196 | 5/2007 |
| WO | 2007/064682 | 6/2007 |
| WO | 2007/064936 | 6/2007 |
| WO | 2008/026970 | 3/2008 |

OTHER PUBLICATIONS

"Design Competition: Runners-Up for the Best Three Designs," EPN, vol. 26, No. 1, 1 pg., 2002.

"IBM and Citizen Watch develop Linux-Based WatchPad," http://wwwlinuxdevices.com/news/NS6580187845.html, 5 pp., 2006.

"MiniMitter® Physiological and Behavioral Monitoring for Humans and Animals," http://www.minimitter.com/Products/Actiwatch, 3 pp., 2006.

"Watch," Wikipedia, 6 pp., http://en.wikipedia.org/wiki/Watch, 2006.

Aminian et al., "Physical Activity Monitoring Based on Accelerometry: Validation and Comparison with Video Observation," Medical & Biological Engineering and Computing, vol. 37, No. 2, pp. 304-308, 1999.

Amzica, "Physiology of Sleep and Wakefulness as it Relates to the Physiology of Epilepsy," Journal of Clinical Neurophysiology, American Clinical Neurophysiology Society, 19(6)1, pp. 488-503, 2002.

Ang et al., "Physical model of a MEMS accelerometer for low-g motion tracking applications," 2004 IEEE International Conference on Robotics and Automation, vol. 2, pp. 1345-1351, 2004.

Buchser et al., "Improved Physical Activity in Patients Treated for Chronic Pain by Spinal Cord Stimulation," Neuromodulation, vol. 8, Issue 1, pp. 40-48, Mar. 2005.

Crago et al., "An Elbow Extension Neuroprosthesis for Individuals with Tetraplegia," IEEE Transactions on Rehabilitation Engineering, vol. 6, No. 1, pp. 1-6, Mar. 1998.

(56) References Cited

OTHER PUBLICATIONS

Dejnabadi et al., "Estimation and Visualization of Sagittal Kinematics of Lower Limbs Orientation Using Body-Fixed Sensors," IEEE Transactions on Biomedical Engineering, vol. 53, No. 7, pp. 1385-1393, Jul. 2006.
Dinner, "Effect of Sleep on Epilepsy," Journal of Clinical Neurophysiology, American Clinical Neurophysiology Society, 19(6), pp. 504-513, 2002.
Foerster et al., "Motion Pattern and Posture: Correctly Assessed by Calibrated Accelerometers," Forschungsgrupe Psychophysiologie, Universität Freiburg, Germany, Mar. 2000, 28 pp.
Foldvary-Schaefer, "Sleep Complaints and Epilepsy: The Role of Seizures, Antiepileptic Drugs and Sleep Disorders," Journal of Clinical Neurophysiology, American Clinical Neurophysiology Society, 19(6), pp. 514-521, 2002.
Fourcade et al., "Modeling Phase Transitions in Human Posture," Studies in Perception and Action VII, Sheena Rogers & Judith Effken (eds), Lawrence Erlbaum Associated, Inc., pp. 99-103, 2003.
Giansanti et al., "The development and test of a device for the reconstruction of 3-D position and orientation by means of a kinematic sensor assembly with rate gyroscopes and accelerometers," IEEE Transactions on Biomedical Engineering, v. 52, No. 7, pp. 1271-1277, Jul. 2005.
Goodrich et al., "The Prediction of Pain Using Measures of Sleep Quality," Pain Digest, 8:23-25, 1998.
Heinz et al., "Using Wearable Sensors for Real-time Recognition Tasks in Games of Martial Arts—An Initial Experiment," Institute for Computer Systems and Networks (CSN), UMIT—University of Health Systems, Medical Informatics and Technology Hall in Tyrol, Austria, 2006, 5 pp., http://eis.comp.lancs.ac.uk/fileadmin/relate/publication/2006-WearableSensors.pdf.
Hendelman et al., "Validity of Accelerometry for the Assessment of Moderate Intensity Physical Activity in the Field," Medicine & Science in Sports & Exercise, pp. S442-S449, 2000.
Hinckley, K., Pierce, J., Sinclair, M., Horvitz, E., *Sensing Techniques for Mobile Interaction*, ACM UIST 2000 Symposium on User Interface Software & Technology, CHI Letters 2 (2), pp. 91-100.
Husak, "Model of Tilt Sensor Systems," ICECS 2002, $9^{th}$ IEEE International Conference on Electronics, Circuits and Systems, vol. 1, pp. 227-230, 2002.
Karantonis et al., "Implementation of a Real-Time Human Movement Classifier Using a Triaxial Accelerometer for Ambulatory Monitoring," IEEE Transactions on Information Technology in Biomedicine, vol. 10, No. 1, pp. 156-167, Jan. 2006.
Kassam, "2005 EDP Topic "MK4": Tremor Data-Logger for Parkinson's Disease Patients," http://www.ee.ryerson.ca/~courses/edp2005/MK4.html, 3 pp., 2005.
Kerr et al., "Analysis of the sit-stand-sit movement cycle in normal subjects," Clinical Biomechanics, vol. 12, No. 4, pp. 236-245, 1977.
Kiani et al., "Computerized Analysis of Daily Life Motor Activity for Ambulatory Monitoring," Technology and Health Care 5, pp. 307-318, 1997.
Kitchin et al., "Compensating for the 0 g Offset Drift of the ADXL50 Accelerometer," Analog Devices Application Note AN-380, 2 pp.
Lau, "Strategies for Generating Prolonged Functional Standing Using Intramuscular Stimulation or Intraspinal Microstimulation," IEEE Transactions on Neural Systems and Rehabilitation Engineering, vol. 15 No. 2, pp. 273-285, Jun. 2007.
Leiper et al., "Sensory Feedback for Head Control in Cerebral Palsy," Physical Therapy, vol. 61, No. 4, pp. 512-518, Apr. 1981.
Lorussi, "Wearable, Redundant Fabric-Based Sensor Arrays for Reconstruction of Body Segment Posture," IEEE Sensors Journal, vol. 4, No. 6, pp. 808-817, Dec. 2004.
Mathie et al., "A Pilot Study of Long-Term Monitoring of Human Movements in the Home Using Accelerometer," Journal of Telemedicine and Telecare 10:144-151, Jun. 2007.
Mathie et al., "Determining Activity Using a Triaxial Accelerometer," Proceedings of the Second Joint EMBS/BMES Conference, Houston, TX, pp. 2481-2482, Oct. 23-26, 2002.
Mattmann et al., "Recognizing Upper Body Postures Using Textile Strain Sensors," Proceedings Eleventh IEEE International Symposium on Wearable Computers, ISWC, pp. 29-36, 2007.
Mendez et al., "Interactions Between Sleep and Epilepsy," Journal of Clinical Neurophysiology, American Clinical Neurophysiology Society, 18(2), pp. 106-127, 2001.
Paraschiv-Ionescu et al., "Ambulatory System for the Quantitative and Qualitative Analysis of Patients Treated with Spinal Cord Stimulation," Gait and Posture, vol. 20, Issue 2, pp. 113-125, Oct. 2004.
Slyper et al., "Action Capture with Accelerometers," Eurographics/ACM SIGGRAPH Symposium on Computer Animation, Carnegie Mellon University, 7 pp., 2008.
Smith et al., "How do sleep disturbance and chronic pain inter-relate? Insights from the longitudinal and cognitive-behavioral clinical trials literature," Sleep Medicine Reviews, YSMRV 286, pp. 1-14, 2003.
Smith et al., "Presleep cognitions in Patients with Insomnia Secondary to Chronic Pain," Journal of Behavioral Medicine, vol. 24, No. 1, pp. 93-114, 2001.
Emmanuel Munguia Tapia, "Activity Recognition from Accelerometer Data for Videogame Applications," http://alumni.media,mit.edu/~ emunguia/html/videogames.htm, 7 pp., Dec. 2, 2003, printed Oct. 1, 2009.
Trolier-Mckinstry et al., "Thin Film Piezoelectrics for MEMS," Journal of Electroceramics, v. 12, No. 1-2, pp. 7-17, Jan./Mar. 2004.
Tuck, "Implementing Auto-Zero Calibration Technique for Accelerometers," Freescale Semiconductor Application Note AN3447, 5 pp., Mar. 2007.
Tuisku, "Motor Activity Measured by Actometry in Neuropsychiatric Disorders," Department of Psychiatry, University of Helsinki, Helsinki, Finland, 115 pp., 2002.
Vega-Gonzalez, "Upper Limb Activity Monitoring," Arch Phys Med Rehabil, vol. 86, pp. 541-548, Mar. 2005.
Velten et al., "A New Three-Axis Accelerometer," Sensor '99-$9^{th}$ Int'l Traide Fair and Conference for Sensors/Transducers & Systems, Nürnberg, Germany, May 18-20, 1999, Sensor '99 Proceedings II, A 5.2, pp. 47-52, 1999.
PCT/US09/49071: International Search Report and Written Opinion dated Apr. 7, 2010, 17 pp.
U.S. Appl. No. 12/815,834, filed Jun. 15, 2010, Gerber et al.
U.S. Appl. No. 12/433,856, filed Apr. 30, 2009, Skelton et al.
U.S. Appl. No. 12/433,750, filed Apr. 30, 2009, Skelton et al.
U.S. Appl. No. 12/433,103, filed Apr. 30, 2009, Skelton et al.
U.S. Appl. No. 12/433,632, filed Apr. 30, 2009, Skelton et al.
U.S. Appl. No. 12/433,558, filed Apr. 30, 2009, Skelton et al.
U.S. Appl. No. 12/433,623, filed Apr. 30, 2009, Skelton et al.
U.S. Appl. No. 12/433,854, filed Apr. 30, 2009, Skelton et al.
U.S. Appl. No. 12/433,749, filed Apr. 30, 2009, Skelton et al.
U.S. Appl. No. 12/433,855, filed Apr. 30, 2009, Skelton et al.
U.S. Appl. No. 12/433,501, filed Apr. 30, 2009, Skelton et al.
U.S. Appl. No. 12/433,520, filed Apr. 30, 2009, Skelton.
U.S. Appl. No. 12/433,551, filed Apr. 30, 2009, Davis et al.
U.S. Appl. No. 12/433,588, filed Apr. 30, 2009, Skelton et al.
U.S. Appl. No. 12/433,599, filed Apr. 30, 2009, Skelton et al.
U.S. Appl. No. 12/433,442, filed Apr. 30, 2009, Skelton et al.
U.S. Appl. No. 12/433,756, filed Apr. 30, 2009, Panken et al.
U.S. Appl. No. 12/433,808, filed Apr. 30, 2009, Skelton et al.
U.S. Appl. No. 12/433,725, filed Apr. 30, 2009, Skelton et al.
U.S. Appl. No. 12/433,530, filed Apr. 30, 2009, Skelton et al.
U.S. Appl. No. 12/433,325, filed Apr. 30, 2009, Skelton et al.
U.S. Appl. No. 12/433,373, filed Apr. 30, 2009, Skelton et al.
U.S. Appl. No. 12/433,651, filed Apr. 30, 2009, Skelton et al.
U.S. Appl. No. 12/433,673, filed Apr. 30, 2009, Skelton et al.
U.S. Appl. No. 12/433,785, filed Apr. 30, 2009, Davis et al.
U.S. Appl. No. 12/433,827, filed Apr. 30, 2009, Skelton et al.
U.S. Appl. No. 12/433,848, filed Apr. 30, 2009, Skelton et al.
U.S. Appl. No. 12/433,840, filed Apr. 30, 2009, Skelton et al.
U.S. Appl. No. 12/433,839, filed Apr. 30, 2009, Skelton et al.
U.S. Appl. No. 12/433,803, filed Apr. 30, 2009, Skelton et al.
U.S. Appl. No. 12/433,815, filed Apr. 30, 2009, Skelton et al.
U.S. Appl. No. 12/433,684, filed Apr. 30, 2009, Skelton et al.
U.S. Appl. No. 12/771,854, filed Apr. 30, 2010, Skelton.
U.S. Appl. No. 12/433,017, filed Apr. 30, 2009, Skelton et al.
U.S. Appl. No. 12/433,004, filed Apr. 30, 2009, Panken et al.

(56) References Cited

OTHER PUBLICATIONS

U.S. Appl. No. 12/548,227, filed Aug. 26, 2009, Skelton et al.
U.S. Appl. No. 12/433,029, filed Apr. 30, 2009, Panken et al.
U.S. Appl. No. 12/432,993, filed Apr. 30, 2010, Panken et al.
U.S. Appl. No. 12/769,461, filed Apr. 28, 2010, Sahasrabudhe et al.
U.S. Appl. No. 12/769,391, filed Apr. 28, 2010, Sahasrabudhe et al.
U.S. Appl. No. 12/769,484, filed Apr. 28, 2010, Panken et al.

* cited by examiner

| Posture ~200 | Amplitude ~202 | Pulse Width ~204 | Electrode Combinations ~206 | ... | Therapy Parameter X ~208 |
|---|---|---|---|---|---|
| Face Up | $A_{Fu}$ | $W_{Fu}$ | $E_{Fu}$ | | $P_{Fu}$ |
| Face Down | $A_{Fd}$ | $W_{Fd}$ | $E_{Fd}$ | | $P_{Fd}$ |
| Right Side | $A_R$ | $W_R$ | $E_R$ | | $P_R$ |
| Left Side | $A_L$ | $W_L$ | $E_L$ | | $P_L$ |
| ⋮ | ⋮ | ⋮ | ⋮ | | |

FIG. 7

BLENDED POSTURE STATE CLASSIFICATION AND THERAPY DELIVERY

RELATED APPLICATIONS

The following application claims priority to provisionally-filed U.S. patent application entitled "Posture State Detection System and Method", Patent Application Ser. No. 61/080,049 filed Jul. 11, 2008, which is incorporated herein by reference in its entirety.

The current application includes subject matter related to the following patent applications, which are incorporated herein by reference in their entireties:

"Posture State Classification for a Medical Device" Ser. No. 12/433,004 filed on even date herewith;

"Posture State Classification for a Medical Device" Ser. No. 12/432,993 filed on even date herewith;

"Reorientation of Patient Posture States for Posture-Responsive Therapy" Ser. No. 12/433,623 filed on even date herewith; and "Posture State Detection Using Selectable System Control Parameters" Ser. No. 12/433,029 filed on even date herewith.

TECHNICAL FIELD

The invention relates to posture detection techniques, and more particularly, to medical devices that detect posture states.

BACKGROUND

A variety of types of medical devices are used for chronic, e.g., long-term, provision of therapy to patients. As examples, pulse generators are used for provision of cardiac pacing and neurostimulation therapies, and pumps are used for delivery of therapeutic agents, such as drugs. Typically, such devices provide therapy continuously or periodically according to parameters. For instance, a program comprising respective values for each of a plurality of parameters may be specified by a clinician and used to deliver the therapy.

It may be desirable in some circumstances to activate and/or modify the therapy based on a patient state. For example, the symptoms such as the intensity of pain of patients who receive spinal cord stimulation (SCS) therapy may vary over time based on the activity level or posture of the patient, the specific activity undertaken by the patient, or the like. It is desirable to be able to detect and classify the state of the patient accurately so that this classification may be used to activate and/or select a therapy that is most efficacious for that state.

SUMMARY

According to one aspect of the disclosure, techniques are provided for classification of a posture of a patient. Therapy may be provided in response to the posture classification. Alternatively, some other response may be taken in response to the posture classification. In one embodiment, posture classification is performed using multiple posture definitions. Each such definition may describe a posture in terms of a defined posture vector, which may be a vector in three-dimensional space. Posture classification occurs by comparing a detected posture vector, which is a vector describing the patient's current posture, to each of the defined posture vectors of the posture definitions.

In one specific embodiment, comparison of a detected posture vector to a defined posture vector yields a similarity value (also referred to as a "similarity"). This similarity indicates how similar the detected posture vector is to the defined posture vector. In one exemplary embodiment, the similarity may be a cosine of an angle between the detected posture vector and a defined posture vector. Other types of similarities are possible, including those that relate to distance measurements such as a Euclidean distance, a city-block distance, and so on.

In one embodiment, the similarities may each be mapped to a respective weighting factor. This mapping is accomplished using a selected weighting function, which may be a graph, an equation, or some other relationship that maps a similarity to a weighting factor value.

After weighting factors are obtained for multiple ones of the defined posture vectors, the weighting factors may be normalized relative to one another. This produces a weighting of all of the defined posture vectors relative to one another. Each of the normalized weighting factors may be conceptualized as describing a percentage of the patient's detected posture vector that is attributable to a respective defined posture vector. Thus, in much the same way a secondary or tertiary color can be described in terms of some proportion of one or more primary colors, the patient's detected posture vector may be "broken down" into, and described in terms of, constituent components comprising the defined posture vectors. The normalized weighting factors thereby provide a description of the detected posture vector and the patient's current posture. In one instance, this description may be presented as an array of the normalized weighting factors corresponding to the defined posture vectors.

According to another aspect, the normalized weighting factors may be used to derive a therapy parameter for use in delivering therapy to the patient. In particular, each normalized weighting factor may be used to weight a parameter value (e.g., a pulse amplitude) that is associated with the respective defined posture vector. If the patient's detected posture vector is determined to be very similar to a defined posture vector based on the similarity value, the corresponding normalized weighting factor may be close to "one" such that the therapy parameter value for that defined posture vector will be the primary consideration in determining how therapy is delivered to the patient. In contrast, if the patient's detected posture vector is very dissimilar to a particular defined posture vector, the corresponding normalized weighting factor may be selected as being zero or close to zero. In this case, the therapy parameter value associated with this dissimilar posture will play little or no part in determining how therapy is provided to the patient. The weighted parameter values may be used to determine a blended parameter value for use in delivering therapy to the patient. For instance, the blended parameter value may be derived as the sum of the weighted parameter values obtained using the normalized weighting factors.

The weighting factors may be used to describe the patient's posture over time. For instance, the weighting factors may be averaged over a time period T. Time-averaged weighting factors may be normalized relative to one another, and then used to determine the portion of time period T that is considered attributable to a respective defined posture vector.

As discussed above, similarity values and weighting factors are derived by comparing a detected posture vector to each of multiple defined posture vectors in a set of such vectors. The set of defined posture vectors used for this purpose may include all defined posture vectors in use in the system, or some selected subset of such defined posture vectors. For instance, the subset may be selected to include only those defined posture vectors associated with postures that are thought to be most likely occupied by the patient. This determination may be based on information specific to the patient, if desired. Alternatively, the subset may be limited to those defined posture vectors considered to be most important for therapy delivery or for patient analysis and diagnosis. Other considerations may be taken into account when selecting the subset of defined posture vectors that are used to classify the patient's posture in the foregoing manner.

The above discussion focuses on using similarities and weighting factors to classify a patient's posture. These techniques may likewise be applied to classification of a patient's activity state. A patient's activity state may relate to overall activity (e.g., footfalls), velocity of motion, acceleration of motion, or some other measure of activity. As was the case with posture definitions, activity state definitions may be created to define various activity states in which the patient may be classified. Such definitions may be expressed in terms of defined activity parameters (e.g., ranges of activity) in much the same way the posture definitions were expressed using defined posture vectors.

To classify a patient's activity state, a detected activity parameter that is indicative of the current activity state of the patient may be received from a sensor. This detected activity parameter may be compared to multiple defined activity parameters included in multiple activity state definitions. Each such comparison yields a respective similarity value representing how similar the detected activity parameter is to the defined activity parameter. A similarity value may be mapped to a respective weighting factor using a weighting function. The weighting factors for all of the defined activity parameters may then be normalized relative to one another. The normalized weighting factors may be used to describe the patient's current activity state. For instance, these normalized weighting factors may be presented in an array of values, each of which may be conceptualized as representing a percentage of the patient's detected activity parameter that is attributable to a respective defined activity parameter.

The normalized weighting factors may be employed to determine a therapy parameter for use in delivering therapy to a patient. In particular, each normalized weighting factor may be used to weight a respective parameter value (e.g., a pulse amplitude) that is associated with the respective defined activity state. The weighted parameter values may be used to determine a blended parameter value for use in delivering therapy to the patient.

According to another similar approach, posture state definitions may be employed that specify at least one of a posture and activity state of a patient. These posture state definitions each include defined parameter values that may be compared to detected parameter values that indicate a current posture state of the patient. Based on this comparison, similarity values may be derived that are then used to obtain weighting factors. The weighting factors may be normalized and used to describe the current posture state of the patient. They may further be used to derive information describing the patient's posture state over time. They may also be utilized to derive therapy parameter values for delivering therapy to a patient in a manner similar to that described above.

In one embodiment, the disclosure relates to a method of obtaining a detected parameter value for use in classifying a posture state of a patient. Multiple posture state definitions are obtained, each being associated with a defined parameter value and a therapy parameter value. For each of selected ones of the posture state definitions a similarity between the detected parameter value and the associated defined parameter value is determined. A blended therapy parameter value is determined based on multiple ones of the similarities and associated therapy parameter values. Therapy is delivered to the patient according to the blended therapy parameter value.

According to another aspect, a system is described that includes a sensor to provide a detected parameter value indicative of a posture state of a patient, and a storage device to store posture state definitions, each posture state definition being associated with a defined parameter value and a therapy parameter value. The system further includes a processor to perform the steps of determining a similarity between the detected parameter value and each of selected ones of the defined parameter values associated with selected ones of the posture state definitions, and determining a blended therapy parameter value for use in delivering therapy to the patient based on the similarities and on the therapy parameter values associated with the selected ones of the posture state definitions.

A storage medium storing executable instructions to cause a processing circuit to perform method steps is also disclosed. In one embodiment, the steps include receiving a detected parameter value indicative of a posture of a patient, obtaining multiple posture definitions describing defined postures, determining multiple similarities, each describing how similar the detected parameter value is to a defined parameter value of a respective posture definition. For each of the posture definitions, a weighted therapy parameter value is obtained that is based on the similarity determined for the posture definition and a therapy parameter value associated with the posture definition. A blended therapy parameter value is obtained based on the weighted therapy parameter values.

Another method of the disclosure comprises obtaining from a sensor carried by a patient a signal indicative of a posture of the patient. The signal is compared to each of multiple posture definitions to obtain multiple similarities, each describing how similar the posture is to a respective posture definition. A classification of the posture is provided that includes the multiple similarities. Care is provided to the patient via a medical device based on the classification.

The details of one or more embodiments of the disclosed techniques are set forth in the accompanying drawings and the description below. Other features, objects, and advantages of the disclosed mechanisms will be apparent from the description and drawings, and from the claims.

BRIEF DESCRIPTION OF THE DRAWINGS

FIG. 7 is a table that lists example postures and associated therapy parameters.

Figure 1:
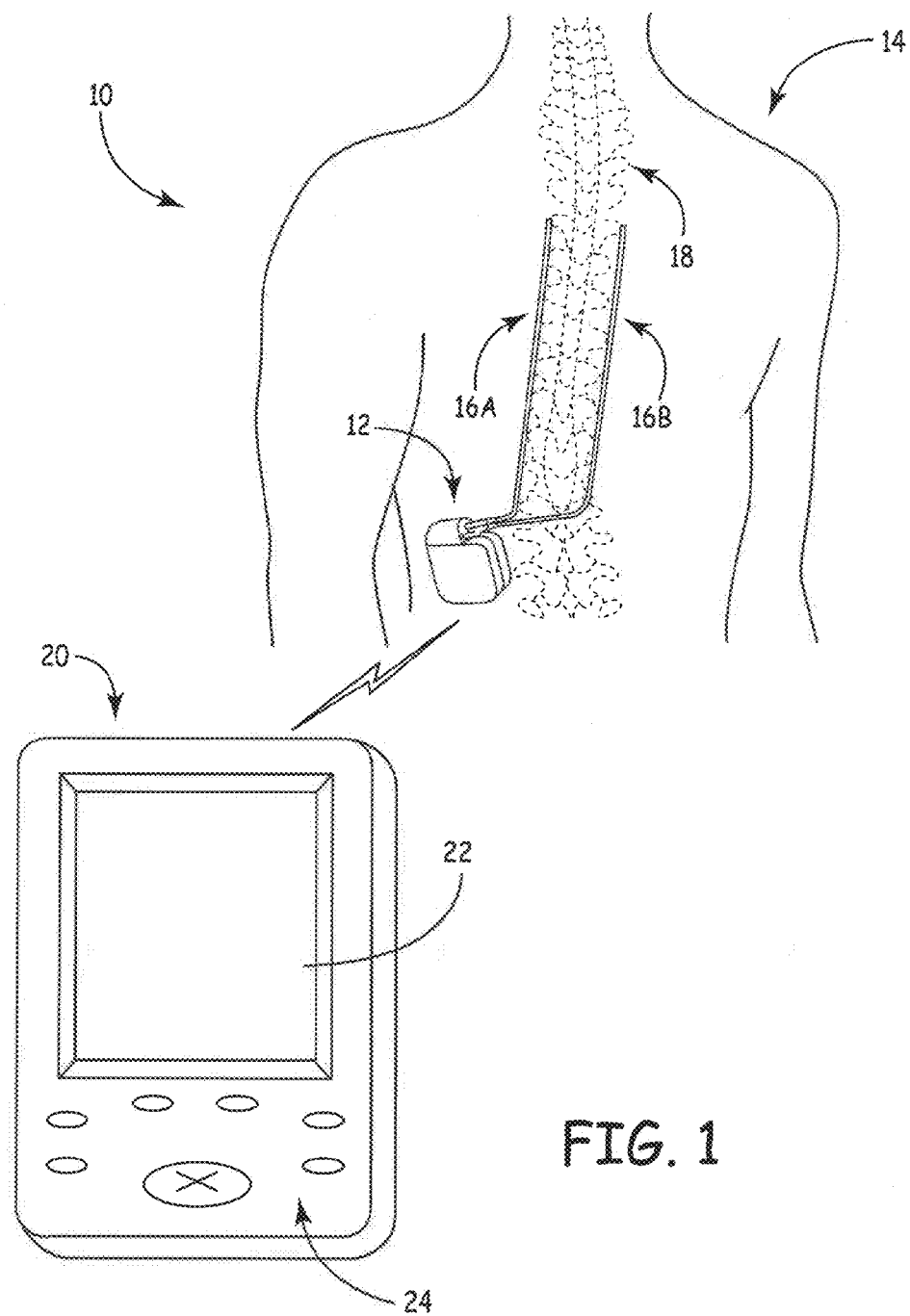
FIG. 1 is a conceptual diagram illustrating an example system that facilitates the definition and classification of posture states according to the disclosure.

The drawings are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION

Techniques described herein relate to classifying a patient's posture state and then delivering a therapy based on the classification. In one embodiment, classification is performed by comparing a detected posture vector that is indicative of the patient's posture with one or more other vectors. These one or more other vectors (hereinafter "defined posture vectors") are each associated with previously-defined postures. Based on the results of this comparison, a similarity is determined between the detected posture vector and each of the one or more defined posture vectors. A similarity is a metric that indicates how similar the detected posture vector is to a respective one of the defined posture vectors. Together, these similarity metrics describe the patient's current posture. These similarity metrics may further be used to determine the therapy to deliver to a patient, as will be described below.

According to some embodiments of the disclosure, a medical device, e.g., an implantable medical device (IMD), includes or is coupled to a sensor that senses a posture. The sensor may be a three-axis accelerometer such as a piezoelectric and/or micro-electro-mechanical (MEMs) accelerometer. The sensed posture may then be used to determine the therapy adjustment.

For example, the IMD may store a table or other data structure that contains records. Each such record may contain therapy information associated with each of the defined postures. The IMD may automatically sense the current posture of the patient and/or changes in the posture of the patient. This sensed information may be employed to reference the table or other data structure that contains the therapy information. An appropriate therapy may thereby be selected that provides the most efficacious results based on the patient's current posture as it relates to the defined postures.

Often times, when a detected posture vector is compared to defined posture vectors, the detected posture vector will not exactly correspond to any of the defined posture vectors. That is, the detected posture vector will lie "in between" multiple ones of the defined posture vectors in three-dimensional space. As an example, a patient may be transitioning from one posture to another, with the patient's current position not matching any of the defined postures. In some systems, the patient's posture would be classified as Undefined in these type of situations. As a result, the therapy to be delivered to the patient may be undetermined.

According to some embodiments of this disclosure, a patient's posture is not categorized as Undefined in the foregoing manner when the current posture does not meet the exact requirements of a defined posture. Instead, the patient's posture is always described using similarity metrics, each of which quantifies how similar the patient's posture is to a respective defined posture. These similarities may be used to select weighting factors. Therapy parameters values associated with the one or more defined posture are scaled by the respective weighting factors to determine a "blended" therapy parameter value for use in delivering therapy to the patient. That is, the therapy parameter value that is selected is derived by weighting the therapy parameter values associated with one or more defined postures. The therapy parameter values that are given the most weight are those associated with the postures to which the patient's current posture is the most similar. In this manner, an appropriate therapy may be delivered to a patient even if the patient's posture does not exactly correspond to a defined posture.

Examples of therapies that may be delivered using techniques presented in the current disclosure include electrical stimulation or the delivery of therapeutic agents. Electrical stimulation may be used, for example, to treat patients that suffer from chronic back pain, leg pain, or other pain that cannot be treated through other methods. As a patient changes posture state, which may involve changes in position and/or activity, the stimulation may need to be adjusted in order to maintain efficacy.

According to an example of the current disclosure, if a patient transitions from one posture to another, blended therapy techniques may be used to generate similarities, each being associated with a respective defined posture. These similarities are used to select weighting factors that are employed to scale various parameter values, such as amplitudes of stimulation pulses, widths of stimulation pulses, rates at which the pulses are delivered, and/or other parameter values.

As a specific example, assume postures P1 and P2 are defined. These postures are associated with therapy parameter values that include pulse amplitudes A1 and A2, respectively. When the patient is detected to be in posture P1, electrical stimulation therapy is delivered using a pulse amplitude of A1, and when the patient is in posture P2, therapy is delivered using a pulse amplitude of A2.

Next, assume the patient is detected to be in an intermediate posture during transition from posture P1 to posture P2. Respective similarity values may be derived to determine how close the patient is to each of these two postures. These similarities may be used to derive respective weighting factors $\omega_1$ and $\omega_2$ for each of these postures. The weighting factors are, in turn, used to determine a pulse amplitude for use in delivering therapy while the patient is in this transition phase. This amplitude may be a function of $\omega_1$, $\omega_2$, A1, and A2, for instance. Various techniques and approaches are discussed in detail below.

FIG. 1 is a conceptual diagram illustrating an example system 10 that facilitates the definition and classification of posture for delivery of therapy according to the disclosure. In the illustrated example, system 10 includes an IMD 12, which is implanted within a patient 14, and which delivers neurostimulation therapy to patient 14.

IMD 12 delivers neurostimulation therapy to patient 14 via therapy connections 16A and 16B ("therapy connections 16"), which may be leads carrying electrodes, for instance. Therapy connections 16 may, as shown in FIG. 1, be implanted proximate to the spinal cord 18 of patient 14, and IMD 12 may deliver SCS therapy to patient 14 in order to, for example, reduce pain experienced by patient 14. However, the disclosure is not limited to the configuration of therapy connections 16 shown in FIG. 1 or the delivery of SCS therapy. For example, one or more therapy connections 16 may extend from IMD 12 to the brain (not shown) of patient 14, and IMD 12 may deliver deep brain stimulation (DBS) therapy to patient 14 to, for example, treat tremor, Parkinson's disease, or epilepsy. As further examples, one or more therapy connections 16 may be implanted proximate to the pelvic nerves, stomach, or other organs (not shown) and IMD 12 may deliver neurostimulation therapy to treat incontinence, gastroparesis, sexual dysfunction or other disorders.

Further, as discussed above, the disclosure is not limited to embodiments in which IMD 12 delivers neurostimulation therapy. For example, in some embodiments, IMD 12 may additionally or alternatively be coupled to one or more catheters or other substance delivery devices to deliver one or more therapeutic substances to patient 14, e.g., one or more drugs.

In exemplary embodiments, IMD 12 functions under the control of one or more programs. A program includes one or more parameters that define an aspect of posture classification and/or detection according to that program.

In exemplary embodiments, IMD 12 may initiate actions in response to information within a record. For instance, a plurality of records may be stored in a table or other data structure. Each such record may describe at least one posture and an associated action that is to be taken in response to detection of this posture state. When IMD 12 detects a posture, IMD 12 may initiate the action that is indicated by the information in the record for that posture. This action may involve delivery of therapy according to a particular program, group of programs and/or a set of parameters. This action may alternatively or additionally involve providing some notification and/or recording some information for use in analyzing a patient's state.

In the illustrated example, system 10 also includes a programming device 20, which may, as shown in FIG. 1, be a handheld computing device. Programming device 20 allows a user such as a patient or a clinician to interact with IMD 12. Programming device 20 may, for example, communicate via wireless communication with IMD 12 using radio-frequency (RF) telemetry techniques, or any other techniques known in the art.

Programming device 20 may, as shown in FIG. 1, include a display 22 and a keypad 24 to allow the user to interact with programming device 20. In some embodiments, display 22 may be a touch screen display, and the user may interact with programming device 20 via display 22. The user may also interact with programming device 20 using peripheral pointing devices, such as a stylus or mouse. Keypad 24 may take the form of an alphanumeric keypad or a reduced set of keys associated with particular functions. In some embodiments, keypad 24 may include an increase amplitude button and a decrease amplitude button to directly adjust stimulation amplitude or another therapy delivery parameter.

In exemplary embodiments, programming device 20 is a clinician programmer used by a clinician to define postures. The defined postures may then be used to detect postures that the patient assumes as the patient goes about daily life. As discussed above, the detected postures may be used to determine a type of therapy to provide to the patient.

Figure 2:
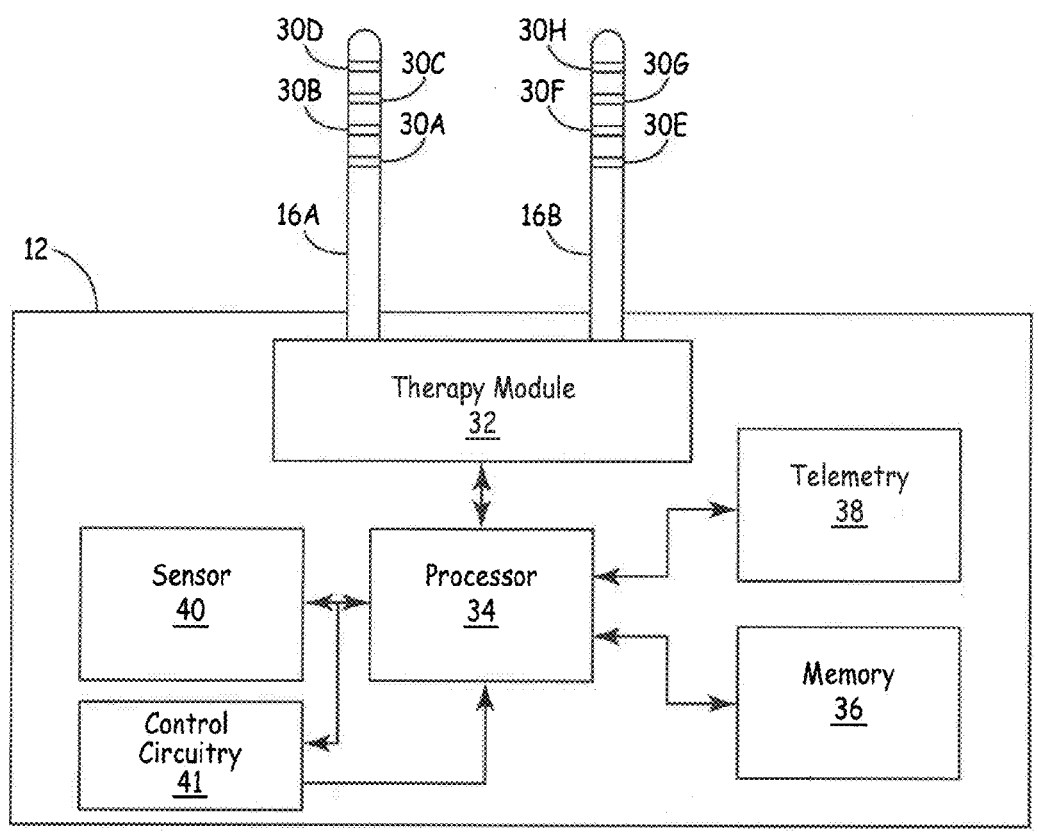
FIG. 2 is a block diagram illustrating one embodiment of an implantable medical device in greater detail.

FIG. 2 is a block diagram illustrating one embodiment of IMD 12 in greater detail. IMD 12 may deliver neurostimulation therapy via therapy connections 16A and 16B. As discussed above, these therapy connections may be leads having one or more electrodes 30A-H (collectively "electrodes 30") or some other therapy delivery connection, such as one or more catheters for delivering a substance to a patient. IMD 12 may be coupled to any number of therapy connections. Therapy connections 16A and 16B are coupled to IMD 12 via therapy module 32. This may be a stimulation pulse generator or a drug delivery controller, for example. Such a therapy module 32 may be coupled to a power source such as a battery.

Therapy delivery may occur under the control of a processor 34. Processor 34 may comprise a microprocessor, a controller, a digital signal processor (DSP), an application specific integrated circuit (ASIC), a field-programmable gate array (FPGA), discrete logic circuitry, or any combination thereof.

Processor 34 may control therapy module 32 to deliver neurostimulation or other therapy according to a selected program. For instance, processor 34 may control therapy module 32 to deliver electrical pulses with the amplitudes and widths, and at the rates specified by the program. Processor 34 may also control therapy module 32 to deliver such pulses via a selected subset of electrodes 30 with selected polarities, e.g., a selected electrode configuration, as specified by the program.

IMD 12 may also include a telemetry circuit 38 that allows processor 34 to communicate with programming device 20. For example, a clinician may select programs, parameters, posture definitions, and associated therapies and actions that are to be transferred to memory 36 of IMD 12. Processor 34 may communicate with programming device 20 to provide diagnostics information stored in memory 36 to a clinician via telemetry circuit 38. Processor 34 may also communicate with a patient programming device to receive from a user such as patient 14 therapy parameter adjustments or other therapy adjustments, as well as commands to initiate or terminate stimulation or other therapy. Telemetry circuit 38 may correspond to any telemetry circuit known in the implantable medical device arts.

IMD 12 further includes a sensor 40 to sense one or more parameters used to detect a posture. In exemplary embodiments, sensor 40 includes a three-axis accelerometer, such as a piezoelectric and/or MEMs accelerometer. In other embodiments, multiple single- or multi-axis accelerometers may be employed in place of one three-axis accelerometer. In yet other examples, sensor 40 may include gyroscopes or other sensors capable of sensing posture. Thus, it will be understood that sensor 40 may comprise more than one sensor.

In exemplary embodiments, sensor 40 is located within a housing (not shown) of IMD 12. However, the disclosure is not so limited. In some embodiments, sensor 40 may be coupled to IMD 12 via additional therapy connections 16 (not shown). The sensor may be located anywhere within patient 14. In some embodiments, IMD 12 may be coupled to multiple accelerometer sensors located at various positions within patient 14 or on the external surface of patient 14, and processor 34 may receive more detailed information about the posture of, and activity undertaken by, patient 14. For example, one or more accelerometers may be located within/on the patient's torso and/or at a position within/on a limb, e.g. a leg, of patient 14. In yet other embodiments, these one or more sensors may communicate wirelessly with IMD 12 instead of requiring one or more leads to communicate with the IMD. For example, sensor 40 may be located external to patient 14 and may communicate wirelessly with processor 34, either directly or via programming device 20.

As previously mentioned, sensor 40 senses one or more parameters that are used to detect a posture. Example postures that may be defined and subsequently detected include the Upright posture, as well as various prone postures including Right Side, Left Side, Face Up, and Face Down, for example. This sensor may, in some embodiments, also detect an activity state related to motion of the patient. The activity state may describe, for example, an overall activity level, an activity level in one or more selected directions, a vector associated with velocity or acceleration, and so on.

IMD 12 also includes a memory 36, which may store programmed instructions that, when executed by processor 34, cause IMD 12 to perform the functions ascribed to IMD 12 herein. Memory 36 may include any volatile, non-volatile, magnetic, optical, or electrical media, such as random access memory (RAM), read-only memory (ROM), non-volatile RAM (NVRAM), electrically-erasable programmable ROM (EEPROM), flash memory, and the like.

FIG. 2 further includes control circuitry 41. This control circuitry is provided in one embodiment to process the analog output of sensor 40. Control circuitry 41 may include discrete components, a microprocessor, a controller, a digital signal processor (DSP), an application specific integrated circuit (ASIC), a field-programmable gate array (FPGA), and/or the like. Control circuitry 41 may operate alone, or in conjunction with processor 34, to process the sensor output for use in detecting a posture state. As an example, control circuitry 41 may process the raw signals provided by sensor 40 to determine activity counts indicative of activity level, velocity along one or more accelerometer axes (as may be obtained by integrating the respective accelerometer signal), and so on, for use in detecting a posture state. This is discussed further below.

Figure 3:
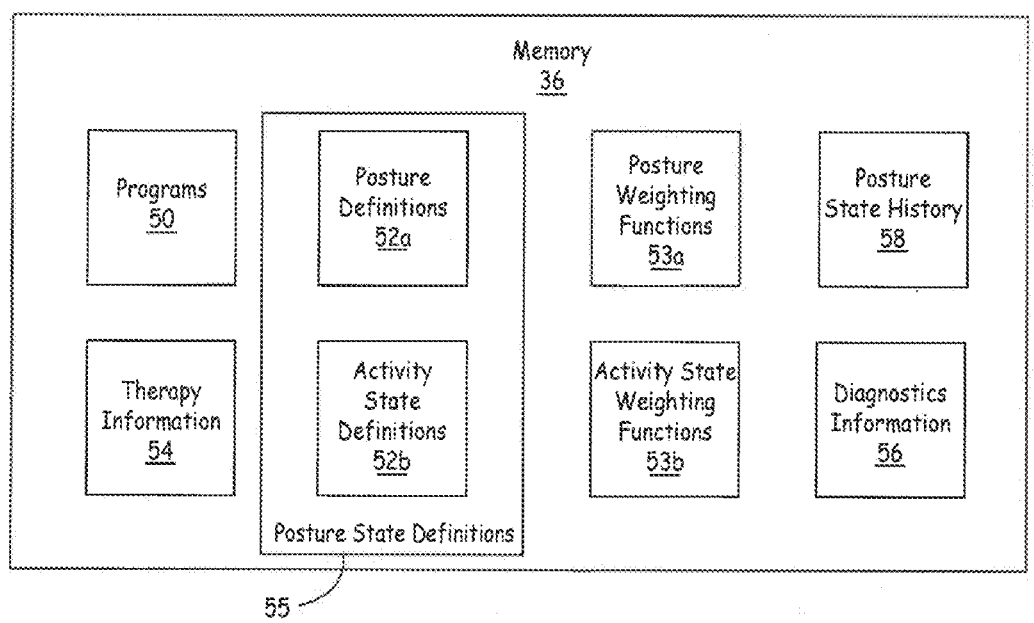
FIG. 3 is a block diagram illustrating an exemplary configuration of a memory of an implantable medical device according to an embodiment of the disclosure.

FIG. 3 is a block diagram illustrating an exemplary configuration of memory 36 of IMD 12. As illustrated in FIG. 3, memory 36 stores programs 50, one or more of which processor 34 may employ to create posture definitions 52a. Posture definitions define the postures in which the patient will be classified. In one embodiment, any number of such postures may be defined, as will be described below.

Memory further stores activity state definitions 52b. As described above, activity states are used to classify a patient's motion. For instance, an activity state of Active may be defined to classify a patient that is undergoing a relatively high level of patient activity. Another activity state may be defined to classify a direction of acceleration or a direction of velocity. By processing output of sensor 40 (e.g., by retaining only AC signal portions and filtering for noise, for instance) and then comparing this output to the activity state definitions, the patient's motion may be classified.

Posture definitions 52a and activity state definitions 52b are each subsets of posture state definitions 55. A posture state definition is a definition that takes into account at least one of a posture and an activity state. Thus, a posture state definition may refer only to a posture (e.g., Upright), only to an activity state (e.g., Active), or to both (Upright and Active).

Posture definitions 52a may be associated with posture weighting functions 53a. These are the relationships that may be used to create blended therapy parameters according to the current disclosure. Similarly, activity state definitions 52b may be associated with activity state weighting functions 53b, which may also be used to create blended therapy parameters. Use of these functions will be discussed further below.

Memory may also store therapy information 54. This information may provide a description of the therapy that should be provided to a patient when the patient is classified as being in any of the predefined postures and/or predefined activity states.

Memory 36 may also store diagnostics information 56 for use in determining how a patient is responding to therapy. In addition to this diagnostics information 56, a patient's posture and activity state may be recorded as posture state history 58. This history data may record, for instance, the patient's current posture information as well as previous posture information. In some cases, this history data may be communicated to an external device such as an external monitor which is used to track a patient's condition.

As discussed above, the signals of sensor 40 may be used to detect a posture. For purposes of this discussion, it will be assumed sensor 40 is a three-axis accelerometer, although sensor 40 could comprise multiple accelerometers instead. Sensor 40 provides a respective signal describing acceleration along each of the x, y, and z axis. These axes will be assumed to be orthogonal, although this need not be the case.

Each of the x-, y-, and z-axis signals provided by sensor 40 has both a DC component and an AC component. The DC components describe the gravitational force exerted upon the sensor, and can thereby be used to determine orientation of the sensor within the gravitational field of the earth. According to the current disclosure, the orientation of the sensor remains relatively fixed with respect to the patient such that the DC components of the x, y and z signals may be utilized to determine the patient's orientation within the gravitational field, and to thereby classify the posture of the patient.

To classify a patient's posture, postures are first defined. According to one exemplary technique, sensor 40 is positioned on, or in, patient 14 in a substantially fixed manner. For instance, the sensor may have been implanted in the patient during a surgical procedure, may have been located on the patient using a transcutaneous procedure, may be temporarily or permanently affixed to an external surface of the patient, or may be carried on the patient's clothing or other articles donned by the patient. The orientation of the sensor relative to the patient is substantially unchanging, at least over some period of time during which posture classification will occur.

Once the sensor is disposed in relation to the patient's body, the patient is asked to temporarily assume a posture. Outputs from sensor 40 are obtained while the patient is in the assumed posture. In the case of a three-axis accelerometer, these outputs may be processed to obtain a vector in three-dimensional space that describes the patient's current posture. Such a vector may be obtained, for instance, by retaining only DC portions of the sensor signals.

Next, the vector, which may be referred to as a defined posture vector, is associated with the posture that the patient has been asked to assume. This association may occur by storing the defined posture vector or some representation thereof with a designation that identifies the posture. Such an association may be stored within a table or another data structure, such as is represented by posture definitions 52a of FIG. 3.

The patient may be asked to assume any number of postures in the foregoing manner. As each posture is assumed, signals are obtained from sensor 40 that are indicative of a defined posture vector. Each such defined posture vector or a representation thereof is associated with a respective patient posture for use later in classifying the patient's posture.

According to one method of classifying a patient's posture, after a defined posture vector is associated with a posture, a tolerance may be selected. The tolerance defines a distance relationship to the posture vector. This distance may define a cone surrounding the posture vector, for instance. Like the defined posture vector, this selected tolerance is associated with the posture. According to one method of posture classification, the defined posture vector and the tolerance may be used to determine whether a patient has assumed the associated defined posture.

The process of obtaining signals from sensor 40 for use in defining postures may be initiated using a programming device such as clinician programming device 20. For instance, a user may utilize programming device 20 to issue a command via telemetry circuitry 38 to IMD 12 when a patient has assumed a desired position. This command causes IMD 12 to obtain signal values from sensor 40, which may be optionally processed by circuitry 41 of IMD and stored in memory 36. These sensor signals may also be uplinked via telemetry circuitry 38 to an external device such as programming device 20 to undergo some of the processing steps.

As previously noted, sensor signals may be associated with an indication (e.g., an alpha-numeric tag, a binary tag, etc.) identifying a posture. The indication may be specified by a user who is employing programming device 20. For instance, a programming device 20 may include a display 22, keypad 24, a touch screen, a peripheral pointing device, and/or other types of user interface mechanisms, as described above. In one embodiment, a user may employ one or more of these mechanisms to capture the sensor output while a patient is in a given posture, provide an indication that identifies the posture, and create an association therebetween. Each such association may be stored in memory of programming device 20, in memory 36 of IMD 12 (e.g., as posture definitions 52*a*), and/or in some other storage facility.

In a similar manner, a user may employ external programming device 20 to specify a tolerance value (e.g., a cone surrounding the vector) and associate that tolerance with a defined posture. This association may likewise be stored in memory of programming device 20, memory 36 of IMD 12, or another storage facility. Techniques for defining a posture vector and creating the above-described associations are described in commonly-assigned Patent Applications entitled "Posture State Classification for a Medical Device", U.S. patent application Ser. Nos. 12/433,004 and 12/432,993 filed on even date herewith.

In the foregoing manner, one or more postures are defined. Each posture is associated with a vector and a tolerance (e.g., a cone surrounding the vector). These defined postures may then be used to classify a patient's position according to one posture classification approach. As may be appreciated, during this classification process, it is important that sensor 40 be maintained in substantially the same position relative to the patient as that sensor was positioned when the posture definitions were originally obtained. This will allow the same sensor coordinate system that was used to define the postures to likewise be used to classify a patient's positions. If the sensor orientation relative to the patient changes, however, as may occur if an IMD 12 rotates with respect to patient 14, recalibration of the defined postures must be performed. This will involve again requiring the patient to assume the postures so that the defined posture vectors associated with the postures may be re-recorded.

In a manner similar to that described above, activity state definitions 52*b* may be created. This may involve requiring the patient to undertake some activity while signals from sensor 40 are processed to obtain an activity parameter that describes the activity. Such an activity parameter may be an overall activity level (e.g., footfalls), a vector indicative of velocity or acceleration involving the activity, some other measure of motion, or any other indication of this patient activity. The parameter values recorded during the activity may be used to create activity state definitions. These definitions may then be used to classify a patient's motion.

Next, specific techniques for classifying a patient's posture are considered. As a patient moves and/or assumes a posture, outputs from sensor 40 are used to obtain measurements that define a detected posture vector indicative of the patient's current posture. According to one technique, this detected posture vector may be compared to one or more of the defined posture vectors of the posture definitions 52*a*. This comparison may be used to determine whether the detected posture vector meets the requirements of any of the posture definitions.

In one specific embodiment, a posture definition may be described in terms of a defined posture vector and a cone surrounding the vector. The patient is classified as being in the defined posture if the detected posture vector for the patient falls within this cone. Such an example is illustrated in FIG. 4.

Figure 4:
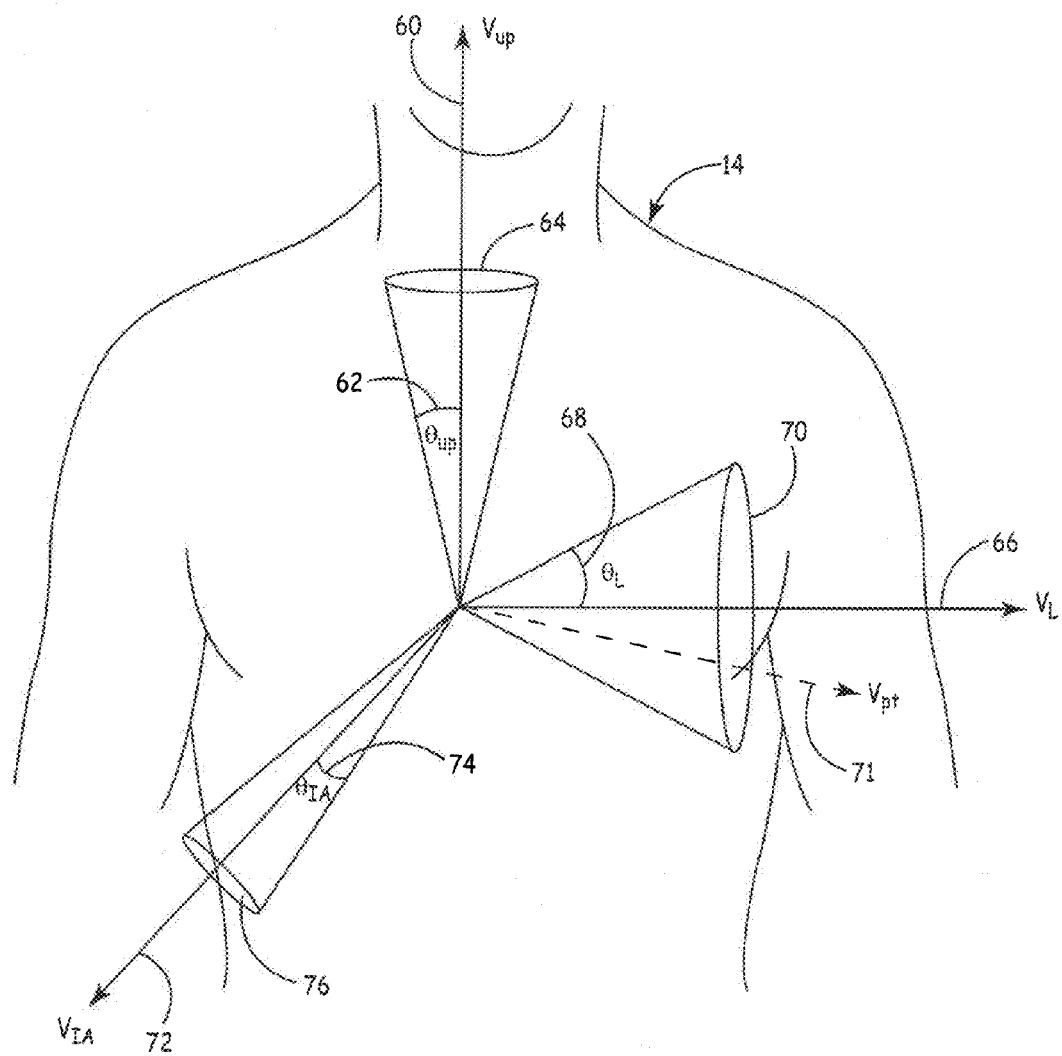
FIG. 4 is a three dimensional graph illustrating one method of defining postures using a sensor such as an accelerometer.

FIG. 4 is a three dimensional graph illustrating one method of defining postures using sensor 40. Sensor 40 (not shown) is disposed in a fixed manner relative to patient 14. When patient 14 is known to be standing upright, sensor 40 will provide outputs that can be processed to obtain a vector $[V_1, V_2, V_3]$ in three-dimensional space which is shown as $V_{Up}$ 60. During a posture definition process, this vector may be associated with an Upright posture, as by storing some indication of the Upright posture along with one or more values identifying this vector. A tolerance may then be selected for this posture that describes a distance relationship to vector $V_{Up}$. In the current example, the tolerance is an angle $\theta_{up}$ 62 which may identify a maximum distance from vector $V_{Up}$ in any direction, as illustrated by cone 64.

During subsequent posture classification according to one type of classification technique, a patient's detected posture vector will be obtained. This detected posture vector may be compared to the defined posture vector $V_{Up}$. If this comparison indicates that the detected posture vector lies within this cone, the patient will be considered to be in the Upright posture. Thus, the patient may be leaning slightly forward, backward, or to either side of, vector $V_{Up}$, while still being categorized as standing so long as the detected posture vector lies within cone 64.

In a similar manner, other posture vectors may be defined. For instance, a vector $V_L$ 66 may be defined that will be used to determine a Left Side posture in which the patient 14 may be classified when he is lying on his left side. In a manner similar to that described above, a tolerance is defined for this vector that involves an angle $\theta_L$ 68. This angle may be used to describe a cone 70 defining a maximum distance from $V_L$ 66. When a detected posture vector lies within this posture cone 70, the patient 14 will be classified as lying on his left side.

Any other one or more postures may be defined in a similar manner. For instance, a vector $V_{IA}$ 72 may be associated with some arbitrary posture in which a patient may be classified when he is lying face down with his head somewhat below his feet. As was the case above, this example shows a tolerance being selected for this posture that involves an angle $\theta_{IA}$ 74 that describes a cone 76 surrounding this vector. If a detected posture vector lies within this cone, the patient will be classified as being in this posture.

In the foregoing manner, any vector may be selected for use in defining a posture. The selected vectors need not be in any particular plane or be in any relationship to any other posture vector. For instance, an Upright posture need not be orthogonal to a Left Side posture. Moreover, postures assumed while the patient is reclining (e.g., Right Side, Left Side, Face Up, Face Down, etc.) need not be co-planar. As still another illustration, a Right Side posture defined to describe a patient lying on his right side may, but is not required to, have a particular relationship (e.g., "opposite") to the Left Side posture. Any number of such postures may be defined.

All of the above examples of posture definitions use a vector and a tolerance. The tolerance may be expressed as a cone. According to posture classification techniques that require use of both the vector and the tolerance involving a cone, a patient may be classified as occupying the associated posture if a sensor reading provides a detected posture vector that is within the cone.

It may be noted that some space may not be included within any posture definition. Specifically, all of the space outside of cones 64, 70 and 76 is excluded from a posture definition in the illustrated embodiment. The size of this space will vary depending on the number of posture definitions in use in the system, as well as the size of the tolerance associated with each posture definition. When a patient's detected posture vector falls outside of the cones, the therapy to be delivered to the patient may be undetermined, as will be described further below.

Figure 5:
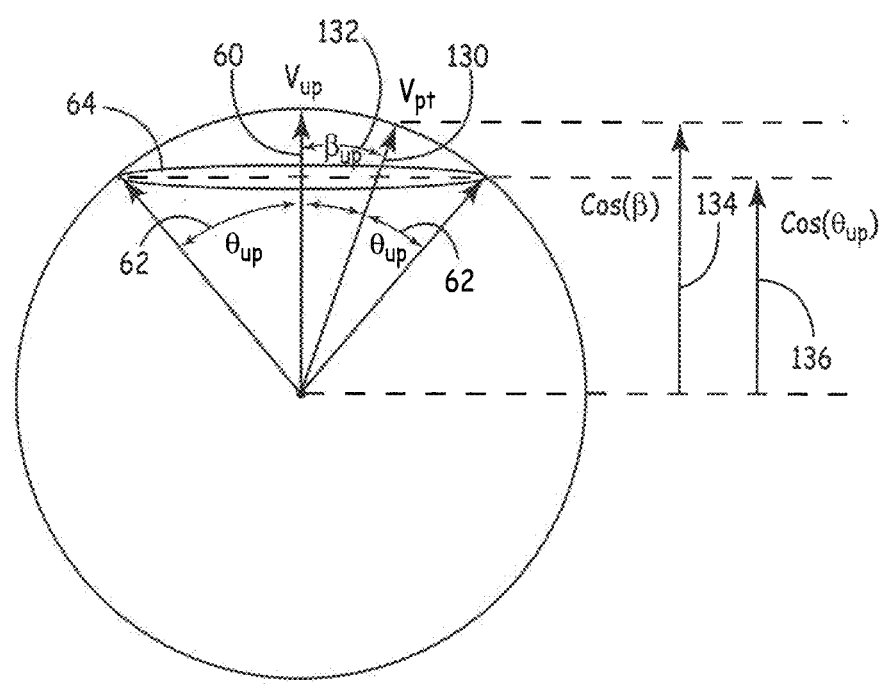
FIG. 5 is a graphical depiction of a posture definition for the Upright posture.

FIG. 5 is a graphical depiction of a technique for classifying a patient's posture using both a defined posture vector and a cone surrounding this vector. The posture definition for this example is defined in terms of defined posture vector $V_{Up}$ 60 and a tolerance described using angle $\theta_{Up}$ 62. As previously described in reference to FIG. 4, the angle $\theta_{Up}$ may be used to describe a cone 64 disposed in relationship to vector $V_{Up}$. In this example, a patient's posture will be classified as being Upright if the detected posture vector $V_{pt}$ 130 for the patient lies within cone 64. This determination may be made using the cosine of angle $\beta_{Up}$ 132, which is the angle between a detected posture vector $V_{pt}$ 130 and $V_{Up}$ 60 as follows:

If $\cos(\beta_{Up}) \geq \cos(\theta_{Up})$, Posture=Upright    (Equation 1)

This is depicted by FIG. 5, which represents the cosine of the angle $\beta$ 132 via arrow 134. The cosine of the angle $\theta_{Up}$ is designated by arrow 136. Since in this case $\cos(\beta_{Up})$ 134 is greater than $\cos(\theta_{Up})$ 132, the patient will be classified as being in the Upright posture.

Assuming for illustration purposes that the Upright posture is the only posture definition that has been created, if the defined posture vector $V_{pt}$ is outside of cone 64 of FIG. 5, the patient's posture cannot be readily classified. This may pose challenges for therapy delivery in an embodiment that relies on defined posture vectors and cones to determine therapy parameters.

Figure 6:
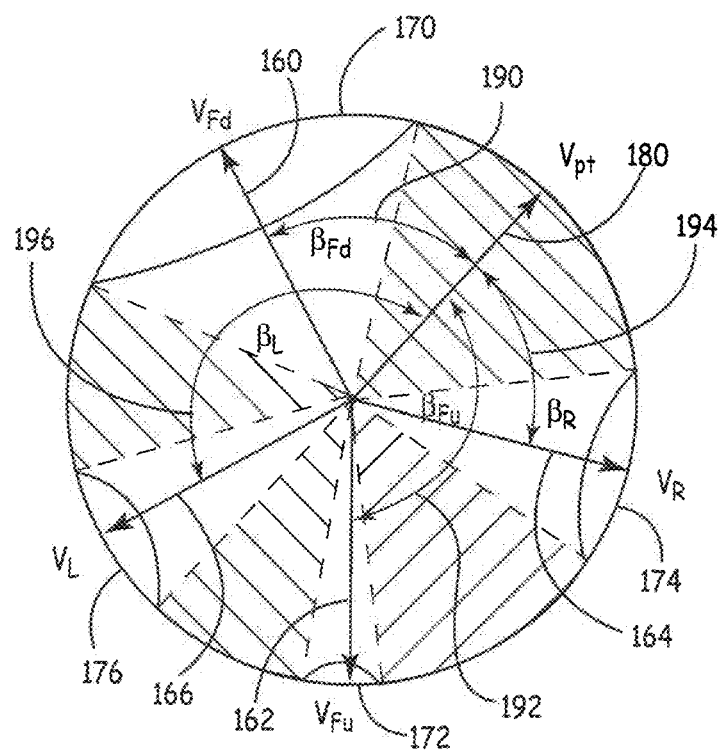
FIG. 6 is another graphical depiction of posture vectors that may be utilized with one embodiment of the disclosure.

FIG. 6 is another graphical depiction of posture vectors that may be utilized to classify a patient's posture. For illustration purposes, it will be assumed that the plane represented by FIG. 6 is that in which the Anterior-Posterior (front-to-back) and Lateral-Medial (side-to-side) axes of the patient also resides. This plane may be occupied by a patient who is lying down, and thus will be used to illustrate exemplary lying down postures. For ease of reference, the various posture vectors associated with the lying down postures are shown to be co-planar, but it will be understood that this need not be the case.

Postures occupied by a patient when lying down may include a Face Down posture assumed when the patient is lying on his stomach, a Face Up posture assumed when the patient is on his back, a Right Side posture assumed when the patient is on his right side, and a Left Side posture assumed when the patient is on his left side. Each of these postures is associated with a respective one of defined posture vectors $V_{Fd}$ 160, $V_{Fu}$ 162, $V_R$ 164, and $V_L$ 166. As shown in FIG. 6, the vectors need not be equidistant from one another, and may be anywhere within three-dimensional space.

Each of the four defined posture vectors $V_{Fd}$ 160, $V_{Fu}$ 162, $V_R$ 164, and $V_L$ 166 described above is associated with a respective cone 170, 172, 174 and 176. The cones need not be of the same size, and in one embodiment, are of a selectable size that may be chosen by a user, such as a clinician who is creating the posture definitions.

As was the case in regards to FIG. 5, in this example, a cone and the associated defined posture vector defines a posture. A patient will be classified as being in a defined posture if a detected posture vector falls within a corresponding cone. For instance, if detected posture vector $V_{pt}$ 180 were located within cone 170 surrounding $V_{Fd}$ 160, the patient will be classified as being in the Face Down posture.

As was the case involving FIGS. 4 and 5, the graph of FIG. 6 includes some space that is not part of any posture definition. This space is represented using diagonal hashing. According to the current example, if a detected posture vector falls within this space, the posture will not be classified as one of the four defined postures. This may pose questions regarding the type of therapy the patient is to receive, as will be discussed further below.

FIG. 7 is a table that lists example postures and associated therapy parameters. Such a table may be stored as therapy information 54 of FIG. 3, for instance. Example postures, shown listed in column 200, correspond to those discussed in regards to FIG. 6. More or fewer defined postures may be utilized, and the postures may include any others instead of, or in addition to, those shown. Columns 202-206 list various therapy parameters that may be used to control how therapy is delivered to a patient when the patient is detected to be in a corresponding posture. For instance, column 202 indicates an electrical stimulation amplitude for use in provided electrical stimulation to the patient. Column 204 indicates a pulse width to be used in delivering electrical stimulation. Column 206 indicates an electrode combination to be used to deliver the stimulation, and so on. Any other parameters may be included in the table instead of, or in addition to, those shown, as represented by columns 208. For instance, the combination of programs used to deliver therapy may be identified in this table, and so on.

The table of FIG. 7 may be created in several ways. It may be provided by a device manufacturer. Alternatively, it may be populated with postures and corresponding parameter values that are provided by a user such as a clinician via a user interface (e.g., the user interface of programmer 20 of FIG. 1). As another possibility, it may be developed dynamically as a patient goes about his daily routine. In this latter case, population of the table may occur as the patient enters therapy adjustments via a patient programmer 20. Such therapy adjustments may be entered into the table of FIG. 7 in association with a posture that the patient occupies contemporaneously with entry of the adjustment, for instance. Such parameters may be periodically updated using patient-provided adjustments or updates provided in some other manner.

Once created, the table of FIG. 7 may be used to deliver therapy to the patient as the patient goes about daily life. As a patient moves about, signals from sensor 40 may optionally be processed in preparation for posture classification. Systems and methods for processing signals in this manner are described in commonly-assigned patent application entitled "Posture State Detection Using Selectable System Control Parameters", U.S. patent application Ser. No. 12/433,029 filed on even date herewith. Processed or unprocessed sensor signals may then be compared to the posture definitions 52a to obtain a posture classification (e.g., "Face Up"). This posture classification may be used to select a therapy parameter, as by using this classification to reference a data structure similar to the table of FIG. 7. The therapy parameters provided in association with the posture classification may be used to determine whether therapy adjustment is needed. The posture classification may also be optionally stored for objectification purposes, which may include determining how well a patient is responding to therapy.

As an example of using posture classification to control therapy delivery, assume a patient has transitioned from being on his Right Side to a Face Up position. In this case, therapy delivery may be changed from that involving pulses having an amplitude and pulse width of $A_R$ and $W_R$, respectively, to that associated with pulses having an amplitude and pulse width of $A_{Fu}$ and $W_{Fu}$, respectively.

It will be understood that although electrical stimulation parameters are shown in the table of FIG. 7, other types of therapies may be delivered in a posture-responsive manner. For instance, parameters associated with drug delivery may be modified based on patient posture. Thus, the example is merely illustrative, and not limiting.

When classifying postures using posture definitions that are described in terms of a defined posture vector and a tolerance (e.g., a surrounding cone), the patient's posture may not meet the requirements of any defined posture. For instance, this occurs in the example of FIG. 6 if the detected posture vector $V_{pt}$ 180 falls within the hashed area. In this case, it may be difficult to determine how to provide therapy to a patient.

The current disclosure provides a different approach to posture classification than that which requires use of vectors and tolerances as shown in FIGS. 5 and 6. This alternative approach may be used alone, or in conjunction with the methods shown in FIGS. 5 and 6, as will be described below.

According to the alternative techniques described herein, a patient's posture may be described in terms of multiple defined postures rather than a single defined posture. These multiple defined postures may include all defined postures, or some subset of all defined postures. The patient's posture is compared to all, or a subset of all, defined posture vectors. Based on each comparison, a similarity value is derived that indicates how similar the patient's posture is to a defined posture vector. Once a similarity value is determined, this value may be used to derive a respective weighting factor ω. Multiple weighting factors may be normalized and employed to describe the patient's posture. This description is provided in terms of multiple ones of the defined postures rather than according to a single posture, as is the case in the methods described in reference to FIGS. 5 and 6.

The weighting factors may further be employed to derive a therapy parameter value for use in delivering therapy to the patient. In particular, each weighting factor may be used to weight a respective parameter value (e.g., a pulse amplitude) that is associated with the respective defined posture. As one example, if the patient's posture is determined to be very similar to a defined posture based on the similarity value, the corresponding weighting factor may be close to "one" such that the therapy parameter value for that posture will be the primary consideration in determining how therapy is delivered to the patient. In contrast, if the patient's posture is very dissimilar to a particular defined posture, the corresponding weighting factor may be selected as being zero or close to zero. In this case, the therapy parameter value associated with this dissimilar posture will play little or no part in determining how therapy is provided to the patient. The weighted parameter values are used to determine the final parameter value for use in delivering therapy to the patient.

As will be appreciated from the more detailed description that follows, the current mechanism does not require the patient's posture to be classified as being in any single posture. Instead, the patient's posture may be described in terms of all, or a subset of all, defined postures. Therapy delivery may be performed according to a continuum of values.

Next, each of the aspects of the current mechanism is considered in more detail. As noted above, the current method utilizes similarity values to describe how similar a patient's posture is to each of multiple defined postures. This may be considered in more detail by returning to FIG. 6. In FIG. 6, the patient's defined posture is represented by detected posture vector $V_{pt}$ 180, which would fall outside of all of the posture definitions if a cone-based approach were being used to classify the posture.

According to the current approach, detected posture vector $V_{pt}$ 180 is not classified in terms of the cones. Rather, a similarity is derived between detected posture vector $V_{pt}$ 180 and each of the four defined posture vectors $V_{Fd}$ 160, $V_{Fu}$ 162, $V_R$ 164, and $V_L$ 166. In one embodiment, the angles $\beta_{Fd}$ 190, $\beta_{Fu}$ 192, $\beta_R$ 194, and $\beta_L$ 196 between the detected posture vector $V_{pt}$ 180 and each of the other defined posture vectors $V_{Fd}$ 160, $V_{Fu}$ 162, $V_R$ 164, and $V_L$ 166 are employed for this purpose. In particular, trigonometric functions (e.g., sines or cosines) of the angles $\beta_{Fd}$ 190, $\beta_{Fu}$ 192, $\beta_R$ 194, and $\beta_L$ 196 may be used to describe how similar $V_{pt}$ is to the corresponding defined posture vectors. For purposes of the current illustration, the cosines of the angles $\beta_{Fd}$ 190, $\beta_{Fu}$ 192, $\beta_R$ 194, and $\beta_L$ between $V_{pt}$ and a respective one of the defined posture vectors $V_{Fd}$ 160, $V_{Fu}$ 162, $V_R$ 164, and $V_L$ 166 are used as similarity values $\sigma_{Fd}$, $\sigma_{Fu}$, $\sigma_R$, and $\sigma_L$, respectively.

In the case of cosines, the larger the cosine of an angle between $V_{pt}$ and a defined posture vector, the more similar $V_{pt}$ is to that defined posture vector. Conversely, if the cosine of the angle is negative, it may be concluded that the angle between $V_{pt}$ and the corresponding defined posture vector is between 90 and 270 degrees, indicating $V_{pt}$ and the defined posture vector are at least somewhat dissimilar. This is the case, for instance, with defined posture vectors $V_L$ 166 and $V_{Fu}$ 162, which point in a somewhat opposite direction to $V_{pt}$ 180 such that cosines of angles $\beta_{Fu}$ 192 and $\beta_L$ 196 will be negative.

Other types of trigonometric functions may be used instead of cosines to express how similar $V_{pt}$ is to a defined posture vector. For instance, a sine of an angle may be used for this purpose. In this case, the similarity value as expressed by the sine of the angle is indirectly proportional to how similar $V_{pt}$ is to the defined posture vector. In yet another scenario, an angle itself may be used to express the similarity, with the size of the angle decreasing as the two vectors become more similar.

As another example, a scalar distance between $V_{pt}$ and a defined posture vector may be determined for use as a similarity. For instance, a city-block distance may be derived between a detected posture vector $V_{pt} = [V_{pt1}\ V_{pt2}\ V_{pt3}]$ and a defined posture vector $V = [V_1\ V_2\ V_3]$ as follows:

$$\sigma = |V_1 - V_{pt1}| + |V_2 - V_{pt2}| + |V_3 - V_{pt3}| \quad \text{(Equation 2)}$$

A variation of this technique provides a Euclidean distance as follows:

$$\sigma = \sqrt{(V_1 - V_{pt1})^2 + (V_2 - V_{pt2})^2 + (V_3 - V_{pt3})^2} \quad \text{(Equation 3)}$$

Yet another technique utilizes a maximum absolute difference $d_\infty(V, V_{pt})$ as follows:

$$\sigma = \max\{|V_1 - V_{pt1}|, |V_2 - V_{pt2}|, |V_3 - V_{pt3}|\} \quad \text{(Equation 4)}$$

Still another approach employs the following:

$$\sigma = \frac{\left(\dfrac{V_1 \cdot V_{pt1} + V_2 \cdot}{V_{pt2} + V_3 \cdot V_{pt3}}\right)^2}{\left(\dfrac{V_1 \cdot V_1 + V_2 \cdot}{V_2 + V_3 \cdot V_3}\right) \cdot} \cdot \text{sign}\left(\dfrac{V_1 \cdot V_{pt1} + V_2 \cdot}{V_{pt2} + V_3 \cdot V_{pt3}}\right) \quad \text{(Equation 5)}$$
$$\left(\dfrac{V_{pt1} \cdot V_{pt1} + V_{pt2} \cdot}{V_{pt2} + V_{pt3} \cdot V_{pt3}}\right)$$

where sign $(x) = 1$ if $x > 0$;
 $= -1$ if $x < 1$; and
 $= 0$ otherwise

Yet another approach utilizes Minkowski (p-norm) distances as a similarity metric. Any type of function that may be used to quantify how similar $V_{pt}$ is to a defined posture vector may be employed to derive similarity values between $V_{pt}$ and each of the defined posture vectors, as described herein.

As previously noted, once similarity values have been determined that express the similarity between $V_{pt}$ and each of the defined posture vectors, these similarity values may be mapped to a respective weighting factor ω. For instance, in the example of FIG. 6, assume similarity values $\sigma_{Fd}$, $\sigma_{Fu}$, $\sigma_R$, and $\sigma_L$ have been derived to describe how similar $V_{pt}$ is to each of the four defined posture vectors $V_{Fd}$ 160, $V_{Fu}$ 162, $V_R$ 164, and $V_L$ 166. A weighting function may then be selected that maps each of these similarity values $\sigma_{Fd}$, $\sigma_{Fu}$, $\sigma_R$, and $\sigma_L$ to a respective weighting factor $\omega_{Fd}$, $\omega_{Fu}$, $\omega_R$, and $\omega_L$. These weighting factors will be used to determine the relative importance of each of the defined posture vectors in classifying $V_{pt}$, and to determine how to weight the therapy parameter values of each of the defined posture vectors when delivering therapy to the patient.

Weighting factors are derived from respective similarity values using one of the posture weighting functions 53a (FIG. 3). In a most simple case, a posture weighting function maps a similarity value to itself. That is, the same value derived for use as the similarity value will also be used as the corresponding weighting factor ω. This type of weighting function may be employed, for instance, when the cosine of an angle is used as the similarity value in the manner described above. In this case, a weighting factor will have a value ranging from −1 to 1. Thus, the weighting factor may be negative some of the time, as will occur when the detected posture vector is in a direction that is at least somewhat opposite to that of a defined posture vector.

For reasons to be discussed below, it may be undesirable to utilize a negative weighting factor. Therefore, another type of weighting function may be utilized that eliminates any negative similarity values. According to this embodiment, the weighting function maps the similarity value to itself if the similarity value is positive, and maps the similarity value to zero if the similarity value is negative. This will essentially disregard all negative similarity values.

The foregoing types of weighting functions are generally used when the similarity value is directly proportional to the similarity between $V_{pt}$ and a defined posture vector. This is the case, for instance, when cosines of angles between the two vectors are used to derive similarity values. When other types of metrics are utilized to derive similarity values, this is not necessarily the case. For instance, when a sine of an angle, an angle itself, or a distance such as a city-block, Euclidean, Minkowski, maximum absolute, or some other distance is used to derive a similarity, an inverse relationship exists between the similarity value and degree of similarity between the two vectors. In other words, as the distance between the vectors increases, the two vectors are less similar to each other. Thus, a weighting function is needed that will address this inverse relationship. For instance, the weighting function may involve subtracting the similarity value from one (e.g., as may be useful in the case of the sine of an angle) or some other maximum similarity value $\sigma_{max}$ and then dividing by $\sigma_{max}$ to obtain the corresponding weighting factor c. This is represented as follows:

$$\omega = \frac{\sigma_{max} - \sigma}{\sigma_{max}} \quad \text{(Equation 6)}$$

Another type of weighting function that may be employed is as follows:

$$\omega = \frac{1}{1 + \sigma^2} \quad \text{(Equation 7)}$$

Like the function of Equation 6, this weighting function maps the similarity value σ to a weighting factor ω when an inverse relationship exists between σ and the similarity between two vectors.

According to an alternative approach, "fuzzy" logic may be employed as weighting functions, as described in relation to FIGS. 8 and 9.

FIGS. 8A-8D are graphs that provide weighting functions used to convert similarity values σ to weighting factors ω. The weighting functions of FIGS. 8A-8D are adapted for use when the similarity values σ are directly proportional to the similarity between a detected posture vector and a defined posture vector.

In these examples, the similarity values, shown along the x axis, range from −1 to 1, although this need not be the case. In all of these examples, when the similarity value is less than 0, indicating that the two vectors being compared are dissimilar, the weighting factor ω (shown along the y axis in each graph) is zero. Thus, these weighting functions will disregard the negative similarity values.

Figure 8A:
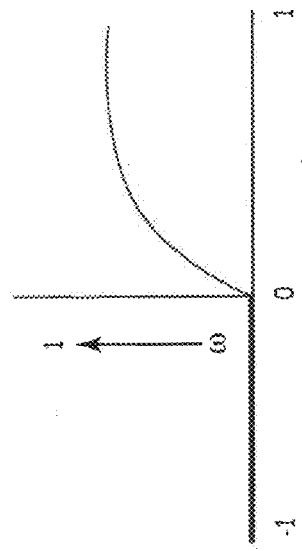
FIGS. 8A-8D are graphs that provide weighting functions used to convert similarity values to weighting factors.
Figure 8B:
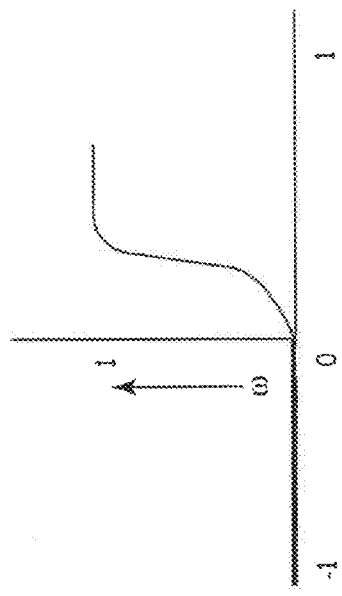
Figure 8C:
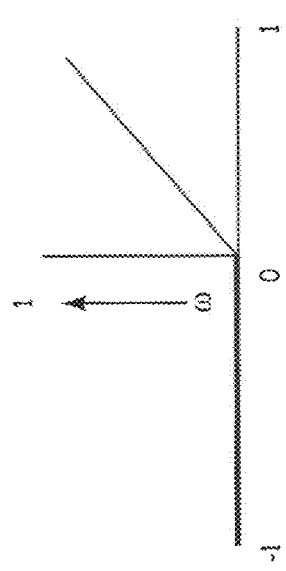
Figure 8D:
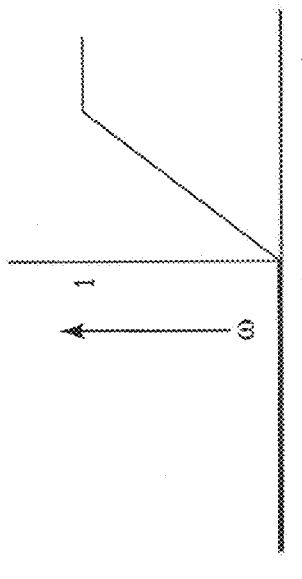

Each of graphs 8A-8D provides different correlations between a positive similarity value and the weighting factors. In the example provided in FIG. 8A, the similarity value is mapped to itself. In FIG. 8B-8D, a positive similarity value is mapped to a different positive weighting factor ranging between 0 and 1. For instance, in FIG. 8D, a similarity value of approximately 0.33 will result in a weighting factor of 1. In contrast, the same similarity value will result in a weighting factor closer to 0.5 when the graphs of FIGS. 8B and 8C are employed. Virtually any type of weighting function may be chosen to map a similarity value to a weighting factor.

Figure 9A:
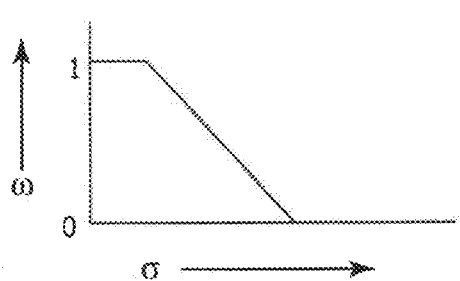
FIGS. 9A-9E are graphs of additional embodiments of weighting functions for converting similarity values to weighting factors.
Figure 9B:
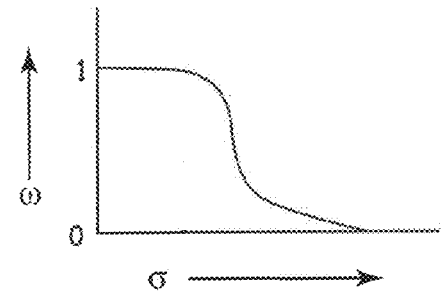
Figure 9C:
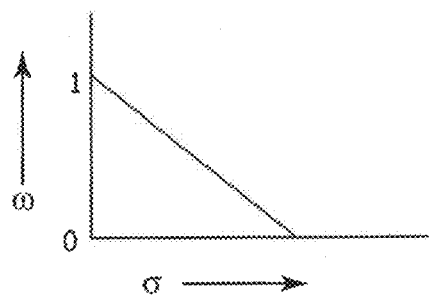
Figure 9D:
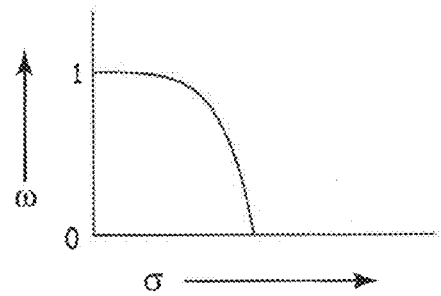
Figure 9E:
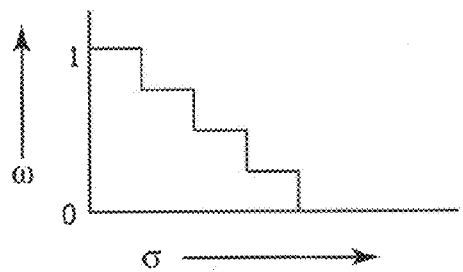

FIGS. 9A-9E are graphs of additional embodiments of weighting functions for converting similarity values to weighting factors. Unlike the examples of FIGS. 8A-8D, these weighting functions are adapted for use when the similarity values are inversely proportional to the similarity between the two vectors that are being compared, as is the case when distance measurements (e.g., city-block, Euclidean, Minkowski, absolute distances, etc.) are being used as the similarity values. In such cases, the similarity values (shown along the X axis) range between 0 and ∞. The weighting factor, shown along the Y axis, will be the largest when the similarity value is 0, indicating the two vectors being compared are substantially the same. In each of the examples of FIGS. 9A-9E, the weighting factors diminish to 0 at some predetermined maximum similarity value which may be different for each of the graphs. Any type of relationship may be used to map the similarity values to the weighting factors. For instance, FIGS. 9A and 9D utilize various non-linear relationships. In FIGS. 9B and 9E, step-like functions are employed. In FIG. 9C, a linear relationship is used.

It will be appreciated that the various weighting functions, including the relationships shown in FIGS. 8A-9D and 9A-9E, are merely exemplary. A substantially infinite number of weighting functions may be contemplated to map similarity values to weighting factors. Such functions may include equations or other relationships in addition to, or instead of, graphs. In one embodiment, the weighting functions may be stored as weighting functions 53a (FIG. 3).

In one embodiment, the weighting function that is in use at any given time within the system may be selected by a user such as a clinician using a programming interface, as may be provided via programmer 20. This weighting function may alternatively be pre-selected by the device manufacturer. In another embodiment, a default weighting function is selected by the device manufacturer, with the user being allowed to override this default using a programming interface. In another scenario, detection of an event or condition within the system may cause re-selection of the weighting function.

Once weighting factors have been obtained, these weighting factors may be normalized. Normalization converts each weighting factor $\omega$ into a corresponding normalized weighting factor $\acute{\omega}$ that conforms to the following requirements:

$$0 \leq \acute{\omega} \leq 1; \text{ and} \qquad \text{(Equation 8)}$$

$$\Sigma \acute{\omega} = 1 \qquad \text{(Equation 9)}$$

The need for normalization can best be considered by example. Assume that two defined posture vectors $V_{Fu}$ and $V_L$ exist within the system. The patient's detected posture vector $V_{pt}$ lies equidistant from these two defined posture vectors. The cosine of the angle between $V_{pt}$ and $V_{Fu}$ is 0.9. Likewise, the cosine of the angle between $V_{pt}$ and $V_L$ is 0.9. Thus, $V_{pt}$ is relatively close to each of $V_{Fu}$ and $V_L$, being separated from each of these vectors by an angle of only about 26° degrees.

Next assume that the cosine value is used as the similarity. Moreover, the mapping function that has been selected corresponds to that shown in FIG. 8A, which maps a positive similarity value to itself for use as the weighting factor. That is, weighting factors $\omega_{Fu}$ and $\omega_L$ for defined posture vectors $V_{Fu}$ and $V_L$, respectively, are both 0.9. As will be appreciated, these values alone do not indicate the relative similarities of $V_{Fu}$ and $V_L$ to $V_{pt}$. Some normalization is required to provide this type of information. This may be accomplished using the following normalization function:

$$\acute{\omega}_i = \frac{\omega_i}{\sum_{i=1}^{N} \omega_i} \qquad \text{(Equation 10)}$$

In this equation, $\acute{\omega}_i$ is the normalized weighting factor for the $i^{th}$ defined posture vector. Normalization is accomplished by dividing the weighting factor for the $i^{th}$ defined posture vector by the sum of the weighting factors for all of the defined posture vectors.

In the current example, a weighting factor $\omega$ of 0.9 is converted to a corresponding normalized weighting factor $\acute{\omega}$ using Equation 10 as follows:

$$\acute{\omega} = \frac{.9}{.9 + .9} = .5.$$

Thus, the normalized weighting factors $\acute{\omega}_{Fu}$ and $\acute{\omega}_L$ for defined posture vectors $V_{Fu}$ and $V_L$, respectively, both have values of 0.5. The detected posture vector $V_{pt}$ may be described in terms of an array [0.5, 0.5] of these normalized weighting factors that corresponds to an array of the defined posture vectors $[V_{Fu}, V_L]$.

As is apparent, the way in which the detected posture vector is described depends on the defined posture vectors that are in use within the system. For instance, assume a user decides to define another posture vector $V_{Fd}$ for use within the system. This new posture vector is separated from $V_{pt}$ by a larger angle (e.g., an angle of about 78°) for which the cosine is above 0.2. Upon re-applying Equation 10 to obtain the three normalized weighting factors for $V_{Fu}$, $V_L$, and $V_{Fd}$, $V_{pt}$ may now be described according to the updated array of normalized weighting factors [0.45, 0.45, 0.1]. Note that all of the normalized weighting factors have a value ranging from 0 to 1, and that the sum is one, thus satisfying the relationships of Equations 8 and 9, above.

The foregoing illustrates how the normalized weighting factors may be obtained and then used to describe a patient's detected posture vector $V_{pt}$. For instance, returning to the foregoing example, it may be appreciated that detected posture vector $V_{pt}$ is quite similar to both of the defined posture vectors $V_{Fu}$ and $V_L$, but is not very similar to the third defined posture vector $V_{Fd}$. Moreover, the degree of similarity to $V_{Fu}$ is equal to that of $V_L$. This is reflected in the array [0.45, 0.45, 0.1] of normalized weighting factors for $V_{pt}$ that corresponds to $[V_{Fu}, V_L, V_{Fd}]$. Each normalized weighting factor may be thought of as representing that portion of the patient's posture that is similar to the corresponding defined posture vector. Thus, in much the same way a secondary or tertiary color can be described in terms of some proportion of one or more primary colors, the patient's detected posture vector $V_{pt}$ may be "broken down" into, and described in terms of, constituent components comprising portions, or percentages, of the defined posture vectors.

In an embodiment wherein negative weighting factors are possible, it is likely desirable to utilize modified normalization techniques. For instance, it may be desirable to utilize an absolute value of a negative weighting factor when deriving the sum that appears in the denominator of Equation 10. Otherwise, a negative value may result for use in the denominator, leading to the unwanted result of a negative weighting factor producing a positive normalized weighting factor. For this reason, and other reasons to be discussed below, it is often preferable to select a weighting function that does not produce negative weighting factors.

According to the current disclosure, the description of $V_{pt}$ will depend on the defined posture vectors that are being used for this purpose. In one embodiment, all of the defined posture vectors in the system may be used. For example, each detected posture vector may be described in terms of an array representing all defined posture vectors in the system. This may be prohibitive, however, if a large number of posture definitions are in use.

According to yet another approach, some subset of all of the defined posture vectors may be selected for use in classifying a patient's posture in the foregoing manner. For instance, the subset may be selected to include only those defined posture vectors for postures that are thought to be most likely occupied by the patient. This determination may be based on information specific to the patient, if desired. Alternatively, the subset may be limited to those defined posture vectors considered to be most important for therapy delivery or for patient analysis and diagnosis. Any one or more of these or additional factors may be used to determine the subset of defined posture vectors to be used to classify a patient's posture in any of the foregoing ways.

In another embodiment, the defined posture vectors that are used to classify a patient's detected posture vector may be selected dynamically. For instance, the patient's detected posture vector may be compared to all defined posture vectors to derive similarity values. A predetermined number K of the defined posture vectors that are determined to be closest, or most similar to (e.g., produce non-negative similarity values), the detected posture vector may be selected for use in classifying the detected posture vector. If this predetermined number K of such defined posture vectors does not exist (e.g., only some smaller number of defined posture vectors produce a positive similarity value), some other selection mechanism may be used. In this latter case, all defined posture vectors resulting in positive similarity values may be selected for use, for instance. The predetermined number K may be programmable, may be a value that is "hard-coded" by device manufacturers, or may be a value selected dynamically based on other considerations, such as the size of storage within the system, the amount of processing capability available within the system, power constraints of the IMD, sensed physiological parameters of the patient, and/or some other value or condition.

Yet another example of the foregoing involves performing some initial comparison of the detected posture vector to determine which defined posture vectors to use in classifying a patient's posture. For instance, assume that the defined posture vectors have been divided into groups. A first group may include all defined posture vectors for standing positions (e.g., Upright, Upright Leaning Forward, Upright Leaning Backward, etc.). A second group may include defined posture vectors associated with prone positions (e.g., Face Up, Face Down, Right Side, Left Side, etc.). A third group may involve defined posture vectors for inverted positions, and so on. Before posture classification is initiated, a patient's detected posture vector is associated with one or more of the groups of the defined posture vectors. Such an association may be performed, for example, based on a comparison between the detected posture vector and a vector that is representative of the defined posture vectors in a corresponding group. After the detected posture vector has been associated with one or more of the groups in this or some other manner, the patient's detected posture vector may be classified using only the defined posture vectors included in the associated groups.

If desired, the subset of defined posture vectors that is used to classify a patient's posture may be changed automatically based on sensed events such as physiological signals received from the patient, commands issued from a programmer, or some other sensed condition. Alternatively, a time of day may prompt re-selection of the defined posture vectors. For instance, a clock of IMD 12 may be utilized to enable a first subset of the defined posture vectors for use in classifying a detected posture vector during the day. A different subset may be enabled for use in classifying the patient's posture at night. In the foregoing manner, any or all of the defined posture vectors may be used to classify a patient's current posture state, and the set of defined posture vectors used for this purpose may change throughout the day, or based on sensed events.

Next, therapy delivery is considered in more detail. As previously discussed, once the normalized weighting factors have been determined, these values may be used to derive a value for a parameter that will be employed to delivery therapy to the patient. Returning to the example discussed in relation to FIG. 7, assume the Face Down, Face Up, Right Side, and Left Side postures have been associated with pulse amplitude values of $A_{Fd}$, $A_{Fu}$, $A_R$, and $A_L$, respectively, as shown in column 202 of FIG. 7. Further assume corresponding normalized weighting factors $\omega'_{Fd}$, $\omega'_{Fu}$, $\omega'_R$, and $\omega'_L$ have been derived in any of the ways discussed above for a detected posture vector $V_{pt}$. These normalized weighting factors may be used to scale (or weight) the amplitudes associated with the four defined posture vectors to obtain a "blended" parameter value that is specific to $V_{pt}$ as follows:

$$A_{Vpt} = \omega'_{Fd} \cdot A_{Fd} + \omega'_{Fu} \cdot A_{Fu} + \omega'_R \cdot A_R + \omega'_L \cdot A_L \qquad \text{(Equation 11)}$$

In a similar manner, blending may be performed for other types of parameters, such as pulse widths, pulse rates, and so on. This blending of therapy parameters allows values used to deliver therapy to be adjusted according to a continuum of values in a smooth manner as a patient's posture changes.

A general approach for deriving a value for a therapy parameter $P_{Vpt}$ using the normalized weighting factors $\omega'_1$-$\omega'_i$ corresponding to defined posture vectors $V_1$-$V_i$ may be summarized as follows:

$$P_{Vpt} = \sum_{i \in I} P_i \cdot \omega' \qquad \text{(Equation 12)}$$

In this equation, the set I includes the set of defined posture vectors selected for use in deriving the parameter $P_{Vpt}$. As discussed above, this set I may contain all defined posture vectors, or some subset of all defined posture vectors that may be selected in virtually any manner, including in some automated manner based on sensed events and/or conditions. The parameter values $P_i$ include those values associated with the defined posture vectors in set I, as are exemplified by the table of FIG. 7. Many other types of parameters may usefully employ the blending techniques described herein.

Upon considering Equations 11 and 12, one may appreciate that large negative weighting factors resulting from defined posture vectors that are "opposite" to a detected posture vector may greatly influence the resulting therapy parameter value $P_{Vpt}$, even "cancelling out" desired therapy levels associated with more similar defined postures. This may not be desirable. Therefore, in one embodiment, weighting functions such as those shown in FIGS. 8A-8D and 9A-9E may be used to ensure that negative similarity values are mapped to weighting factors having values of zero.

Figure 10:
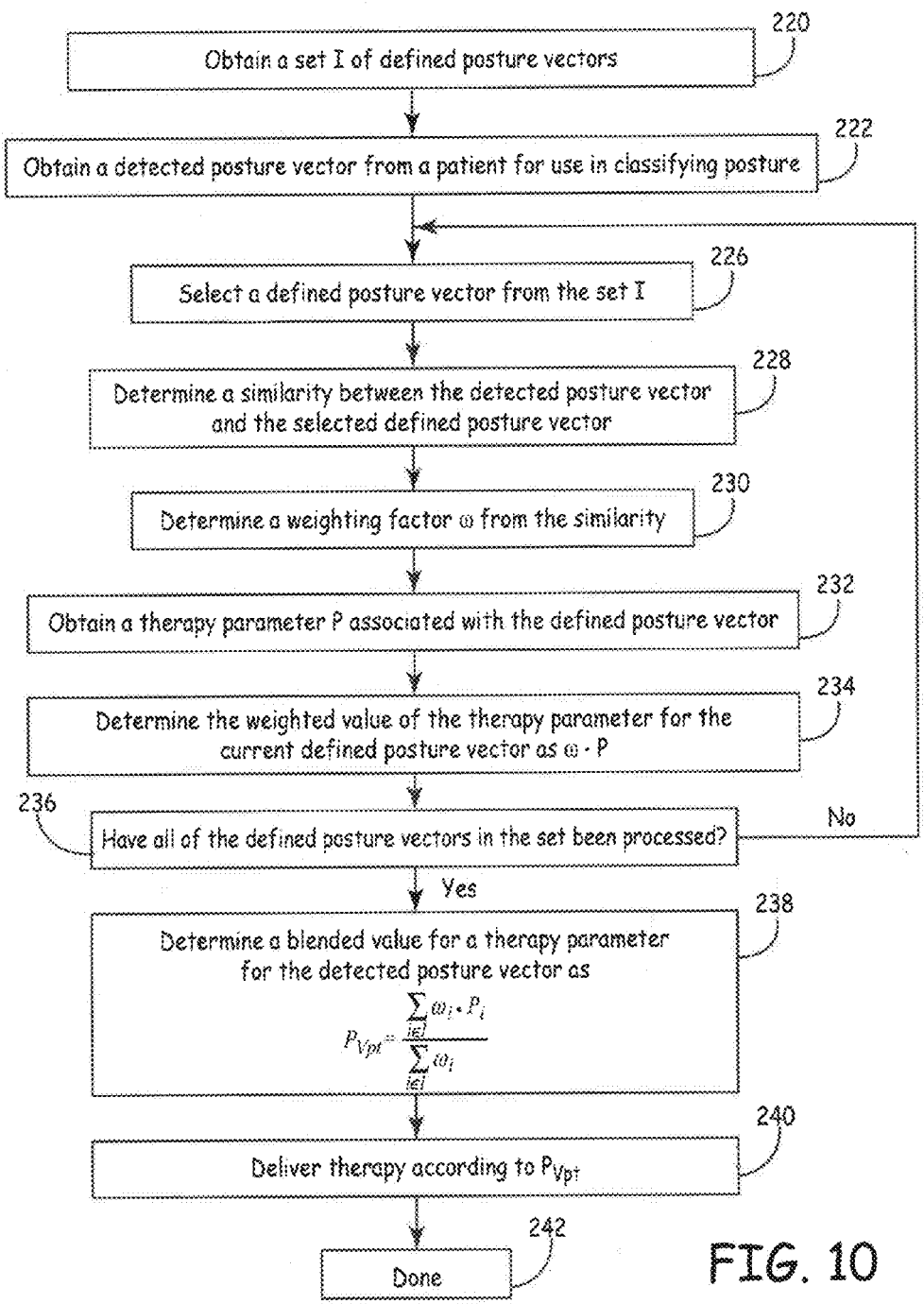
FIG. 10 is a flow diagram illustrating delivery of therapy to a patient according to one embodiment of a blended therapy delivery approach.

FIG. 10 is a flow diagram illustrating delivery of therapy to a patient according to one embodiment of a blended therapy delivery approach. A set I of the defined posture vectors that are to be used to deliver therapy is obtained (220). This set may include all defined posture vectors for all defined postures, or may instead be some subset K of all defined posture vectors. For instance, the subset may involve only those defined posture vectors that are thought to be most likely occupied by the patient, those believed most important for therapy delivery, those selected based on an initial inquiry (e.g., group associations), and so on.

Next, a detected posture vector is obtained from a patient for use in classifying the patient's posture (222). A defined posture vector is selected from the set I of defined posture vectors (226). A similarity between the detected posture vector and the selected defined posture vector is determined (228). This similarity may be an angular distance, a non-angular scalar distance, a trigonometric function of an angle between the two vectors, or some other type of measure of the similarity between the two vectors. In one exemplary instance, the similarity is a cosine of an angle between the two vectors.

Next, a weighting factor ω is obtained from the similarity (230). This weighting factor may be obtained using any of the weighting functions described herein, or any other weighting function. Many such functions may be contemplated. The weighting function that is selected may be patient-specific, may be based on one or more physiological signals measured by the system, or on some other characteristic of the system. In general, a same weighting function will be selected for use in deriving all of the weighting factors that are used to obtain a given blended therapy parameter value. That is, the same weighting function will be selected for use during all iterations of the method of FIG. 10.

A therapy parameter P may be obtained for the defined posture vector that is currently being processed (232). Such a therapy parameter may involve electrical stimulation (e.g., a pulse amplitude, pulse width, stimulation frequency, etc.). Alternatively, the parameter may involve some other therapy such as drug delivery (e.g., drug bolus amount, frequency of drug delivery, etc.). Any type of parameter associated with therapy delivery to a patient that may be adapted for use according to this blended approach may be selected.

A weighted value of the therapy parameter is determined by multiplying the parameter value P by the current weighting factor ω (234). Next, it is determined whether all of the defined posture vectors in set I have been processed (236). If not, execution returns to step 226 where another defined posture vector is selected, and processing steps 228-234 are repeated.

When all of the defined posture vectors in set I have been processed, execution continues to step 238 wherein a value for the blended therapy parameter for the detected posture vector is determined. This blended parameter value, $P_{V_{pt}}$, is determined as follows:

$$P_{V_{pt}} = \frac{\sum_{i \in I} \omega_i \cdot P_i}{\sum_{i \in I} \omega_i} \quad \text{(Equation 13)}$$

Note that the parameter value $P_{V_{pt}}$ is determined by dividing the sum of all of the weighted parameter values $P_i \cdot \omega_i$ obtained during all iterations of step 234 by a sum of all of the weighting factors determined in step 230. This provides the necessary normalization, which could alternatively be performed for each of the weighting factors individually in the manner described above with respect to Equation 10. Therapy may be delivered using this parameter value $P_{V_{pt}}$ (240), and processing is then complete (242). The process of FIG. 10 may be repeated periodically, as when a change in the patient's posture is detected and/or at predetermined time intervals.

Figure 11:
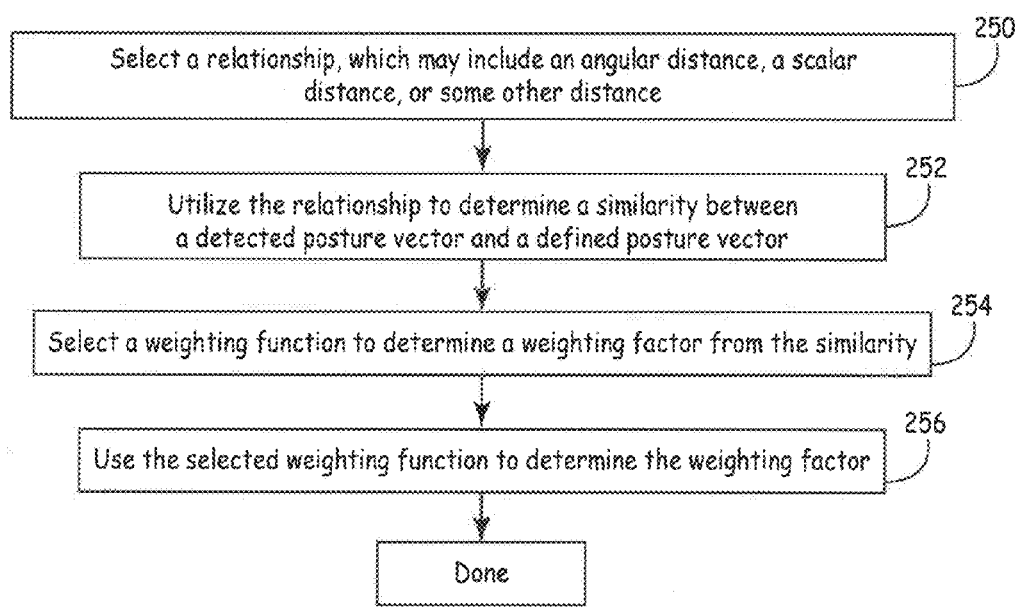
FIG. 11 is a flow diagram illustrating in more detail one exemplary method of determining similarity values and weighting factors.

FIG. 11 is a flow diagram illustrating in more detail one exemplary method of determining similarity values and weighting factors. This method may be used to accomplish steps 228 and 230 of the method of FIG. 10, for instance. According to this approach, a relationship is selected for use in determining a similarity value (250). This may be an angle that expresses distance is degrees, radians, or some other angular measure. Alternatively, this relationship may be a non-angular scalar distance, such as a cosine of an angle, a sine of an angle, a city-block distance, a Euclidean distance, a Minkowski distance, an absolute distance, or some other distance.

The selected relationship is utilized to determine a similarity value between a detected posture vector and a defined posture vector (252). This similarity value describes how close, or similar, the detected posture vector is to the defined posture vector. This similarity value may be directly proportional to the degree of similarity between the two vectors (e.g., cosines), or may instead be inversely proportional to the degree of similarity between the two vectors (e.g., sines, city-block distances, etc.)

A weighting function may next be selected to determine a weighting factor from the similarity (254). Such a function, which may be stored as one of weighting functions 53a (FIG. 3), may be described using an equation, a graph, or some other mechanism that maps a similarity value to a weighting factor. The selected relationship is used to determine the weighting factor (256).

As described above, many methods are available for obtaining a parameter value $P_{V_{pt}}$ for detected posture vector $V_{pt}$. Once a therapy parameter has been determined in any of the foregoing ways, this parameter may be used to adjust the therapy being delivered to the patient. For instance, in the case of amplitude, therapy may be modified from a current amplitude value to the newly-derived, target amplitude in a linear manner, with a slope that will be positive or negative depending on whether the target amplitude is greater than, or less than, respectively, the current amplitude. In another embodiment, the change from an existing amplitude to a new target amplitude may be accomplished exponentially, as may be accomplished using an exponential attack or decay function. In this case, an exponential constant may be utilized. This exponential constant may serve as a positive attack value if the target amplitude value is greater than the current value, or may instead serve as a negative decay value if the target amplitude value is less than the current amplitude value.

The choice as to whether to use a linear or an exponential function to accomplish therapy level transitions may be hard-coded in some embodiments, or selected by a user via a programming interface such as provided on a clinician programmer.

These techniques described herein may be used to accumulate statistical data on the patient's posture states. One type of measure that may prove useful for such analysis is a time average of the similarity values and/or the weighting factors for one or more postures. According to this approach, a time-averaged similarity value σ may be generated for the detected posture vector and a predetermined defined posture vector, as follows:

$$\sigma\_ave = \frac{\sum_{s=1}^{T} \sigma_s}{T} \quad \text{(Equation 14)}$$

Using this approach, the similarity between the patient's detected posture vector and a predetermined one of the defined posture vectors may be determined periodically, as at regular time intervals. The average for T such similarity values obtained over time may be determined according to Equation 14. This metric will provide an indication of how close, or similar, on average, a patient's posture was to the predetermined defined posture vector during a given time period.

As an example of the foregoing, assume a patient's detected posture vector is sampled once per minute. Each such sample of the detected posture vector is compared to the defined posture vector for the Upright posture to determine a similarity value. At the end of an hour, an average may be taken for all T such similarity values (where "T" is "sixty" in this case). This will provide a measure of how similar, on average, the patient's detected posture was to the Upright posture during the hour. This type of average may be derived for any one or more of the defined posture vectors.

The numerator of Equation 14 may be thought of as an accumulator of all similarity values associated with the predetermined defined posture over the hour. This type of accumulator may be used to track a patient's posture with respect to this defined posture vector, if desired. For instance, in the current example, assume for simplicity that each similarity value is 0.5. The sum of all 60 similarity values yields "30", which could be considered a surrogate indication of how much time the patient spent in the Upright posture over the course of the hour. That is, this could be viewed as representing 30 minutes that the patient spent in the Upright posture during this time.

In a similar manner, a time average of a weighting factor may be derived for a predetermined defined posture vector as follows:

$$\omega\_ave = \frac{\sum_{s=1}^{S} \omega_s}{S} \quad \text{(Equation 15)}$$

To derive this average, the patient's detected posture vector may be sampled S times over some time period. Each of these detected posture vector samples is compared to a predetermined one of the defined posture vectors to obtain S similarity values. Each obtained similarity value may be mapped to a respective weighting factor using any of the techniques described above. The average for the S weighting factors may then be determined. This will provide a time average of the weighting factor for the predetermined one of the defined posture vectors over the period of time represented by the S detected posture vector samples.

Returning to the foregoing example, assume that the sixty similarity values derived for the Upright posture over the course of an hour are each mapped to a respective weighting factor using a weighting function. For simplicity, it is assumed that each similarity of 0.5 maps to a weighting factor of 0.5. These sixty weighting factors may be averaged according to Equation 15 above to determine a time-averaged weighting factor of 0.5 that is assigned to the Upright posture over this one-hour period.

It may be noted that the numerator of Equation 15 is an accumulator that tallies all weighting factors associated with the predetermined defined posture (e.g., the Upright posture) over the period of time during which the S weighting factors were derived. Like the accumulator discussed in regards to Equation 14, this accumulated value may be conceptualized as a surrogate measure of the total time spent in the associated posture. For instance, again assume that all sixty weighting factors obtained for the Upright posture during the one hour period have a value of exactly 0.5. Each such weighting factor may be conceptualized as representing one-half minute that the patient occupied the Upright posture during each one-minute sample period. Adding all sixty one-half minute portions that were recorded for the one-hour time period yields thirty minutes of time attributable to the Upright posture. In a similar manner, accumulated times may be calculated for other ones of the defined posture vectors for which weighting factors were determined.

Each of the time-averaged similarity values and time-averaged weighting factors may be normalized in a manner similar to that described above with respect to Equation 10, if desired. For instance, assume a time-averaged weighting value ω_ave is derived for each of K defined postures using Equation 14 set forth above. Each of these values may be normalized as follows:

$$\omega_i'\_ave = \frac{\omega\_ave_i}{\sum_{k=1}^{K} \omega\_ave_k} \quad \text{(Equation 16)}$$

As may be noted, the time-averaged weighting factor for the $i^{th}$ defined posture is divided by the sum of all time-averaged weighting factors for all K defined postures. Similar normalized time-averaged weighting factors may be derived for each of the K defined postures. When all of these normalized values are added together, the result will be "1".

As previously discussed, all postures in use within the system may be normalized with respect to each other. Alternatively, fewer than all such postures may be normalized in this manner.

The normalized time-averaged weightings may be conceptualized as that portion, or percentage, of the patient's posture that is attributable to a particular defined posture during a particular time period. Returning to the foregoing example, assume that the normalized time-averaged weighting factor for the Upright posture over a predetermined period of time is 0.5. This indicates that approximately 50% of all of the weighting used to perform therapy delivery or to classify a patient's posture during this time period is attributable to the Upright posture. Stated otherwise, the therapy parameter values associated with the Upright posture received 50% of the weighting used to derive the therapy parameter values that were actually used to deliver therapy to the patient during this time period.

As discussed above, the normalized time-averaged weightings may be used as a representation of the portion of the time spent in a particular defined posture. For instance, assume again that the normalized time-averaged weighting factor for the Upright posture for some predetermined period of time is 0.5. This may be conceptualized as an indication that approximately 50% of this time period was spent in the Upright posture as opposed to any of the other defined postures being used to calculate the normalized average weighting factors. By multiplying each normalized time-averaged weighting factor $\omega_i$ by a total time T over which the weighting factors were derived, a conceptualization of the total time $T_i$ spent in the $i^{th}$ posture may be derived as follows:

$$T_i = T \cdot \omega_i'\_ave \quad \text{(Equation 17)}$$

Returning to the above illustration, if the normalized time-averaged weighting factor for the Upright posture during a one-hour time period is determined to be 0.5, the total time spent in the Upright posture during this one-hour period may be calculated as one-half of sixty minutes, or thirty minutes. Thus, this is another way to derive a representation of the total time spent in a defined posture over a predetermined time period. Recall that another way to arrive at substantially the same value is to add all of the weighting factors for the defined posture over the predetermined time period. This was as described above in reference to the "accumulator" appearing in the numerator of Equation 15.

Similar time values may be derived for all of the defined posture vectors used to perform the normalization process. This type of data may be stored as posture state history 58 (FIG. 3) if desired. This information may be used to assess the patient's well-being and response to therapy, perform diagnosis, obtain a patient baseline, and so on.

As may be appreciated, the conceptualized time values obtained using Equation 17 will, in all likelihood, not correspond to actual time spent by the patient in any particular defined posture. For instance, the patient will rarely spend time in a position that exactly aligns with the defined posture vector for the Upright posture. Rather, even when the patient is generally upright, the patient is typically leaning slightly in any direction as compared to the exact defined posture vector for the Upright posture. The patient's detected posture will therefore be classified as a "blend" of the Upright posture vector and one or more other defined posture vectors, such as the defined posture vector for Face Down or Face Up, etc. The precise blend is described by the weighting factors. Therefore, a conceptualized time value derived in the manner described with respect to Equation 17 merely provides an indication regarding the amount of the overall "posture blend" that is attributable to a corresponding defined posture vector, and is not necessarily to be viewed as the actual time spent in a defined posture that corresponds to this vector.

Figure 12:
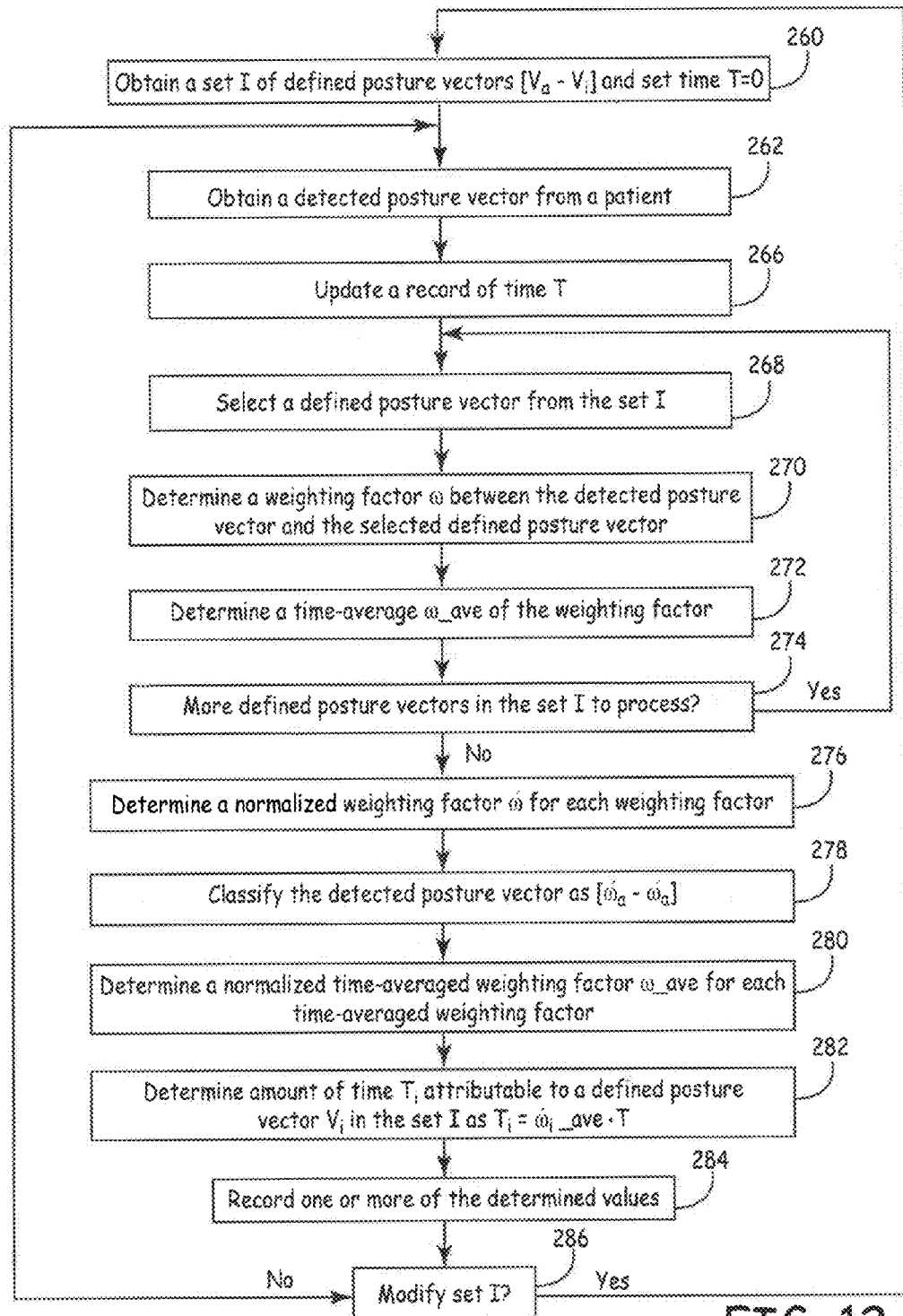
FIG. 12 is a flow diagram of one method of tracking the defined posture vectors to which a patient is closest.

FIG. 12 is a flow diagram of one method of classifying a patient's posture using multiple defined posture vectors. A set I of defined posture vectors is obtained for the defined postures in use within the system (260). This set may be all, or some subset of all, of the defined posture vectors. For instance, the set may include only the K defined posture vectors to which the patient is most likely to be closest. The set may include the subset of defined posture vectors for postures that are considered most important to therapy delivery, or some other method may be used to select a subset of defined posture vectors for this purpose.

A detected posture vector is obtained from a patient for use in classifying the patient's posture state (262). In one embodiment, detected posture vectors may be obtained at a predetermined sampling rate or may instead be obtained at irregular time intervals.

When a detected posture vector is received, a record of the total time T may be updated, where T is the total time over which the posture classification is occurring (266). In embodiments wherein time data is not required, this step may be eliminated.

Next, a defined posture vector is selected from the set I of defined posture vectors $[V_a\text{-}V_i]$ (268). A weighting factor $\omega$ may be determined between the detected posture vector and the selected defined posture vector (270). This step may involve determining a similarity, selecting a weighting function, and obtaining a weighting factor corresponding to the similarity based on the weighting function. In general, a same weighting function will be selected for use in deriving all of the weighting factors that are used during all iterations of the method of FIG. 12.

A time average, $\omega\_ave$, of the derived weighting factor may then be determined, if desired (272). This time average may be obtained by averaging all of the values derived over time T for the weighting factor for the selected defined posture vector, including that value for the weighting factor derived in step 270. This step assumes that such values have been derived and are being retained for this purpose, of course. Derivation of the time average may be performed as shown in Equation 15 above, for instance.

If there are more defined posture vectors in the set I to process (274), processing continues to step 268 where another defined posture vector is selected from set I. Otherwise, if all defined posture vectors in the set have been processed in step 274, processing proceeds to step 276. There, a normalized value $\omega$ for each of the weighting factors is determined. This will result in a weighting factor for each of the defined posture vectors $[V_a\text{-}V_i]$ in set I. The detected posture vector may then be classified as an array $[\omega_a\text{-}\omega_i]$ of the normalized weighting factors (278).

If desired, a normalized value $\omega\_ave$ may likewise be determined for each of the time-averaged weighting factors $\omega\_ave$, if such time-averaged weighting factors are being maintained (280). This may be accomplished according to Equation 16, for instance. The amount of time T attributable to a given defined posture vector $V_i$ in set I may then be determined as $\omega\_ave_i \cdot T$ (282). One or more of the determined values may be recorded (284). Recording of such values will be required, for instance, if averages of the weighting factors are being maintained over time T. Any of the derived values may be retained for analysis, for therapy delivery purposes, for performing diagnostics, for initiating some other type of response, or for some other purpose. If set I is to be modified (286), as may occur automatically based on time of day or some other sensed condition or event, or instead based on user input, execution returns to step 260. Otherwise, processing returns to step 262 where another detected posture vector may be received from the patient. The method of FIG. 12 may continue for a predetermined period of time, until a user stops the process, or until some other detected event occurs.

The foregoing focuses on posture classification based on a patient's body positioning, as may be determined in one embodiment using DC portions of one or more signals generated by sensor 40. According to another aspect, a patient's posture state may alternatively or additionally be classified using AC signal portions of the signal(s) from sensor 40, for instance, which indicates a patient's motion.

As described above, a patient's motion may be classified using activity state definitions 52b (FIG. 3). For instance, an activity state of Active may be defined to classify a patient that is undergoing a relatively high level of patient activity. Another activity state may be defined to classify a direction of acceleration or a direction of velocity.

As is the case with posture definitions, a patient's activity state classification may be used to determine parameter values and/or adjustments (e.g., adjusting therapy upward or downward), or to initiate some other type of response. This may be accomplished using a data structure similar to that shown in FIG. 7 for associating postures with therapy parameters. As was the case with the associations between posture definitions and therapy parameters, such associations between activity state definitions and therapy parameters may be stored along with therapy information 54.

According to one embodiment, blending techniques may be applied to activity state classification in a manner similar to that described above with respect to posture classification. For instance, assume processing of an AC portion of the signal of sensor 40 yields an activity count of between 0 and 100, which may represent footfalls or some other activity measurement, for instance. This activity level range may be used to define activity state definitions, as by associating certain subsets of this range with activity states (e.g., 0-20 is a Low activity state, 20-40 is a Moderate activity state, and so on). Multiple such activity state definitions may be created.

Next, assume a patient's current activity level (that is, a "detected activity level") is measured by sensor 40 and compared to defined activity levels to determine similarity values.

As one example, this may be accomplished by determining a difference between the patient's detected activity level and some activity level associated with the activity level definitions.

As a more specific example, assume a patient's activity level is measured to be "30". This value may be compared to the range 0-20 for the Low activity state, as may be accomplished by comparing a median value of "10" for this range to the detected level of "30". The absolute difference between these two number, or "20", may be used as the similarity value. As another example, the detected activity parameter of "30" may be compared to the closest range endpoint of "20" for the activity state definition, or instead to the farthest range endpoint of "0". Alternatively, some other measure may be used to derive the similarity value. This process may be repeated for the activity state definition that has an activity level range that is greater than the detected activity level. Once these similarity values are determined, these values may be used to determine weighting factors. These weighting factors may be normalized. The patient's activity state may be classified according to an array of such normalized values. The various processing steps shown in FIG. 12 describing posture classification may likewise be applied to classification of activity state.

The foregoing discussion describes activity levels as an example of the types of activity parameters used to determine an activity state. However, activity states may be defined in terms of vectors, such as velocity or acceleration vectors. In such cases, the type of vector processing discussed above in regards to posture classification may be used to classify a patient's activity state.

It may be desirable to determine a therapy parameter value based on activity state. In this case, the blending techniques described herein may be utilized to obtain the value for the therapy parameter based on the weighting factors for the defined activity states.

Figure 13:
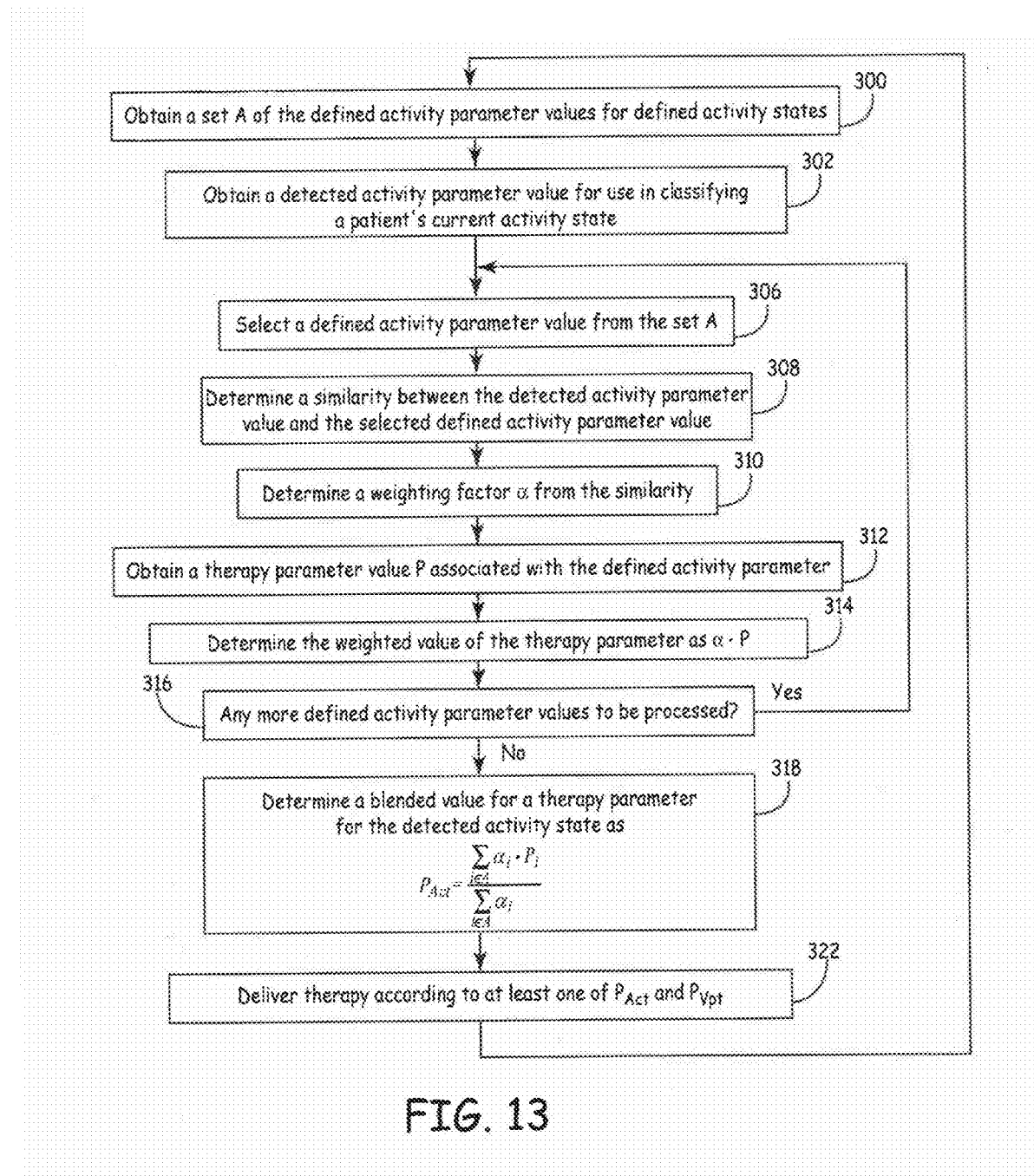
FIG. 13 is a flow diagram illustrating delivery of therapy to a patient according to another embodiment of a blended therapy delivery approach that uses activity state definitions.

FIG. 13 is a flow diagram illustrating delivery of therapy to a patient according to one embodiment of a blended therapy delivery approach that is based on activity state definitions. First, a set A of defined activity parameter values for defined activity states are obtained (300). The defined activity parameter values may involve an activity level (e.g., a measure of footfalls, for instance), a vector indicative of acceleration, velocity, or some other vector indicative of activity, or any other measure of activity and/or motion.

The obtained set A may include a parameter value for all defined activity states, or may instead involve only a subset of all defined activity states. For instance, generally the subset will include only those definitions that are defined in terms of a particular type of activity parameter that is currently being processed. The subset may alternatively or additionally involve only those defined activity states in which the patient is most likely to be engaged, that are most important for therapy delivery, or that are selected on some other basis.

In some cases, it may be desirable to only select a predetermined number of activity parameters for inclusion in set A that are the closest to the detected activity parameter. For instance, in the case of activity levels, the two activity parameters that occupy ranges on "either side" (greater than, and less than) of that detected activity parameter may be selected. In the case of vectored activity parameters, the K closest vectors may be selected in the manner described above, and so on.

Next, a detected activity parameter value is obtained for use in classifying the patient's activity state (302). This detected activity parameter value should be of a similar type as those parameters included in the selected set A so that a meaningful comparison between the detected activity parameter and those parameter values in set A may be obtained. A defined activity parameter value may then be selected from set A (306). A similarity between the detected activity parameter value and the selected defined activity parameter value is determined (308). This similarity may be an angular distance (if the parameters involve vectors), a non-angular scalar distance between the parameters (e.g., an absolute difference), or some other type of measure of how similar the two parameter values are to one another. Any of the various types of similarity mechanisms described herein or otherwise known in the art may be used for this purpose.

Next, a weighting factor α is obtained from the similarity (310). This weighting factor may be the similarity value itself, or may be based on another relationship. As was the case involving postures, the weighting factor may be selected using any weighting function that maps the similarity value to a respective weighting factor.

A therapy parameter P may be obtained for the defined activity parameter value that is currently being processed (312). Such a therapy parameter may involve electrical stimulation (e.g., a pulse amplitude, pulse width, stimulation frequency, etc.). Alternatively, the parameter may involve some other therapy such as drug delivery (e.g., drug bolus amount, frequency of delivery, etc.). Any type of parameter associated with therapy delivery may be utilized.

A weighted value of the therapy parameter for the current activity parameter value is determined as the product α·P (314). If some of the defined activity parameter values remain to be processed (316), execution returns to step 306 where another defined activity parameter is selected.

When all of the defined activity parameters in set A have been processed, processing continues to step 318 wherein a value for the therapy parameter is determined. This therapy parameter value is determined as follows:

$$P_{Act} = \frac{\sum_{i \in A} \alpha_i \cdot P_i}{\sum_{i \in A} \alpha_i} \qquad \text{(Equation 18)}$$

This equation is similar to Equation 13 described above with respect to deriving therapy parameter values using detected posture vectors.

Processing next continues to step 322, where therapy is delivered to the patient based on at least one of $P_{Act}$ and $P_{Vpt}$, where $P_{Vpt}$ is a therapy parameter value that was determined based on the patient's current classified posture. This value may be determined using blending techniques described above.

In one embodiment, $P_{Vpt}$ may be used as a base parameter value, and $P_{Act}$ may be used to determine an adjustment to this base value. For instance, $P_{Act}$ may be scaled (e.g., divided by 10 or 100) and then added to $P_{Vpt}$. Alternatively, $P_{Act}$ may be used as a base parameter value and $P_{Vpt}$ may be used to determine an adjustment to this base value. In yet another embodiment, some other relationship may be utilized to take into account both $P_{Vpt}$ and $P_{Act}$, if desired, as by using weighting factors to determine the relative importance of the two values. In another embodiment, only one of these values may be used to deliver therapy, if desired.

If desired, the process may be repeated periodically by returning to step 300 and processing a newly-acquired detected activity state. For instance, the process may be repeated at the sampling rate of the sensor signal.

As may be appreciated, the methods of FIGS. 10 and 13 may be combined such that the steps related to classifying posture and activity state, and to obtaining blended therapy parameters for one or both of the posture and activity state, are included in a single iteration. In any case, those skilled in the art will recognize that the ordering of the steps of the methods may, in some cases, be rearranged, and some steps may be omitted, within the scope of the disclosure.

As discussed previously, a posture state definition may refer to, or include, a posture definition, an activity state definition, or both. That is, a posture state definition may describe a patient's posture, motion, or posture and motion. Posture definitions 52a and activity definitions 52b are therefore two subsets of posture state definitions 55 (FIG. 3). With this in mind, the methods of FIGS. 10 and 13, which involve posture definitions and activity definitions, respectively, may be generalized as a single method that refers to posture state definitions. This is shown in regards to FIG. 14.

Figure 14:
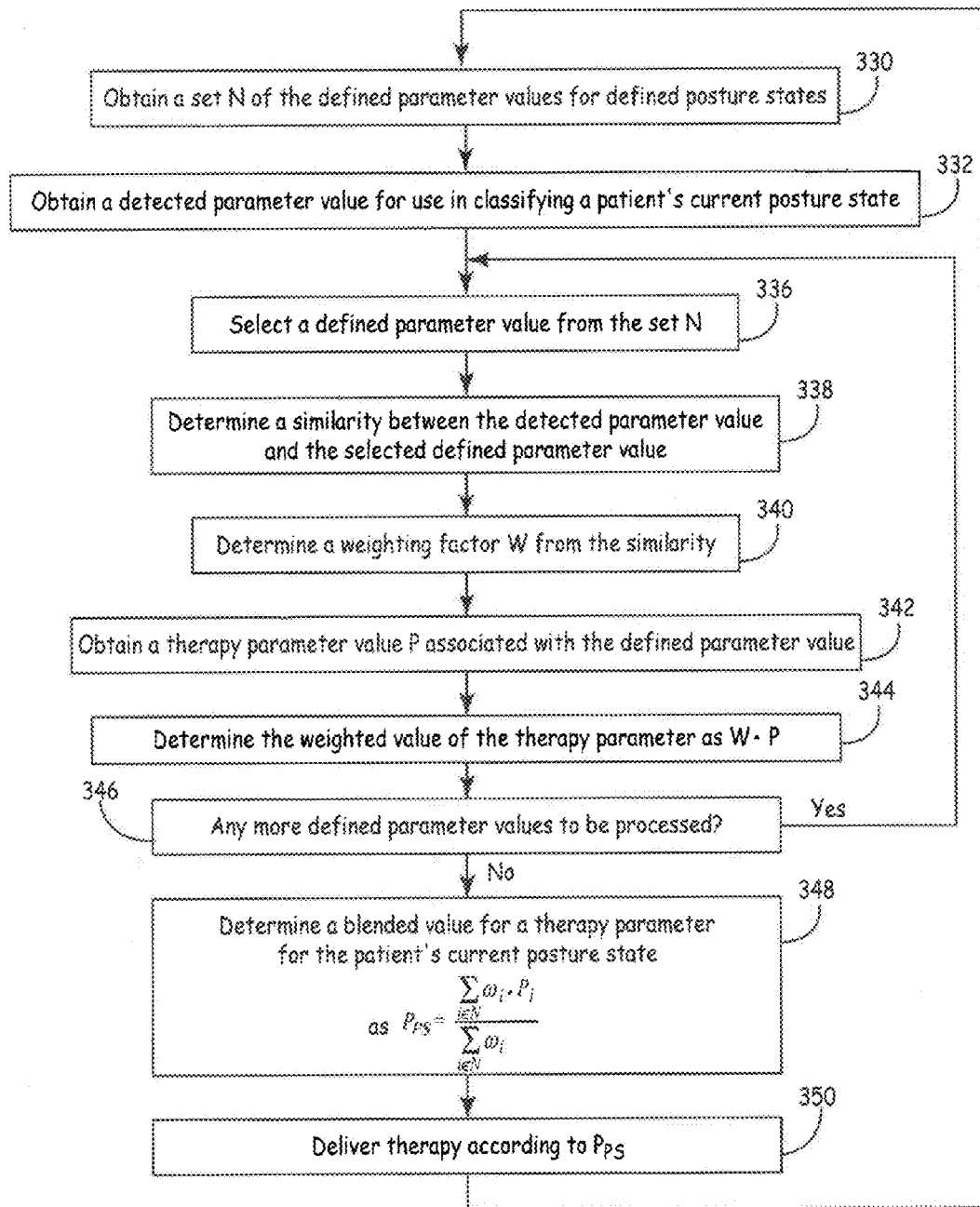
FIG. 14 is a flow diagram illustrating delivery of therapy to a patient according to an embodiment of a blended therapy delivery approach that uses posture state definitions.

FIG. 14 is a flow diagram illustrating delivery of therapy to a patient according to an embodiment of a blended therapy delivery approach that uses posture state definitions. According to this method, a set of N defined parameter values are obtained for defined posture states (330). The defined parameter values may involve vectors, as used for posture definitions or for some activity state definitions. Alternatively, the defined parameter values may involve some other parameter type, such as an activity level parameter used to define activity states. A detected parameter value is then obtained from sensor 40 for use in classifying a patient's current posture state (332). Like the defined parameter values, this detected value may be a vector or some other type of parameter, such as an activity level. To have a meaningful comparison between this detected parameter value and the defined parameter values in set N, all parameters should be of a similar type.

Next, one of the defined parameters from set N is selected (336). A similarity between the detected parameter value and the selected defined parameter value is determined (338). This similarity may be used to determine a weighting factor W (340). Step 340 may involve selecting one of weighting functions 53a, 53b to be used to map the similarity to the weighting factor W. The weighting function that is selected may be patient-specific, may be based on one or more physiological signals measured by the system, may be based on a type of the parameter values that are being considered (e.g., vectors, activity levels, etc.), or may be based on some other characteristic of the system. In general, a same weighting function will be selected for use in deriving all of the weighting factors that are used to obtain a given blended therapy parameter value. That is, the same weighting function will be selected for use during all iterations of the method of FIG. 14.

Next, a therapy parameter value P associated with the defined parameter value is obtained (342). The weighted value of the therapy parameter may next be determined as W·P (344). If any more defined parameter values are to be processed from set N (346), processing returns to step 336. If no more defined parameter values are to be processed, execution continues to step 348, where the blended therapy parameter value for the patient's current posture state is determined as follows:

$$P_{PS} = \frac{\sum_{i \in N} W_i \cdot P_i}{\sum_{i \in N} W_i} \quad \text{(Equation 19)}$$

where i is the index value of the defined parameters from the set N, the numerator is the sum of all of the weighted values determined in step 344, and the denominator is the sum of all of the weighting factors determined in step 340. Therapy may then be delivered according to this blended therapy parameter value $P_{PS}$ (350). This method may be repeated each time a next detected parameter value is obtained, as from sensor 40. Thus, this method may be repeated at the sampling rate of system, or at some other interval, if desired.

In the foregoing manner, blending techniques may be used to classify a patient's posture state in terms of multiple defined posture states rather than in terms of a single defined posture state. This leads to more meaningful classification in some circumstances.

These blending mechanisms may further be used to derive therapy parameters based on defined postures, defined activity states, or both. This smoothes changes in therapy that will occur as a patient transitions from one defined posture to the next, and/or from one defined activity state to the next.

According to one alternative embodiment, the techniques described herein may be with some other posture classification technique, such as that shown in FIG. 6. In FIG. 6, posture definitions involve both a detected posture vector and an associated tolerance (e.g., a cone surrounding the vector). A detected posture vector may be compared to each of the posture definitions to see whether it is within the associated tolerance. If so, the patient is classified as being in the corresponding defined posture, and therapy is delivered accordingly. For instance, $V_{pt}$ 180 (FIG. 6) may be determined to fall within cone 170 such that the patient is classified as being in the Face Down posture. Therapy is therefore provided according to the therapy parameters associated with the Face Down posture. Using one embodiment of the disclosure, if the detected posture vector does not meet the requirements of any of the defined postures, (e.g., the detected posture vector falls within the hashed region of FIG. 6) the patient's posture may be classified using the blended approach described herein. Therapy may then be delivered to the patient based on a blended approach that uses a combination of multiple therapy parameter values associated with multiple ones of the defined postures. This hybrid technique utilizes blending in some situations and a tolerance-based approach (e.g., use of cones) in other situations.

A similar technique may be applied to activity. That is, a detected parameter that describes a current activity state of the patient may be compared to defined parameter ranges for defined activity states. If the detected parameter falls within one of the defined parameter ranges, the patient is classified as being in the associated activity state, and therapy is delivered according to a tolerance-based approach. Otherwise, if the detected parameter falls outside of all ranges, the blended approach may be utilized wherein the patient's activity state is classified based on multiple defined activity states, and therapy is delivered using a blended technique.

Alternative embodiments may be contemplated wherein blending for postures and/or activity states are selectively enabled. Such enabling may occur based on monitored system conditions, physiological signals received from the patient, commands received from a user, and any other type of event that may be used to trigger use of blending.

While the above-description has applied the blending techniques disclosed herein to classifying posture states and adjusting therapy delivery, it will be appreciated that the posture state classifications may be used to initiate other types of responses. As an example, it may be desirable to automatically issue some type of notification if the time-averaged normalized weighting factor for some defined posture (e.g., some prone posture) exceeds a certain value over a period of time (e.g., exceeds 0.75, for example). For instance, a time-averaged normalized weighting factor for a prone posture of 0.75 could indicate that roughly 75% of the patient's time during the monitored period was attributable to this prone posture, which may indicate a problem with the patient's therapy, or may even indicate a patient fall.

Other types of responses may likewise be initiated based on the posture state classification. For instance, a new therapy regimen could be selected. Any other type of response associated with the patient, the patient's care, the patient's therapy system, and so on, may be initiated additionally or in the alternative based on the posture state classification mechanisms herein disclosed.

Those skilled in the art will recognize that various modifications may be made to the systems, methods, and techniques described herein. For instance, the methods described by the various flow diagrams may be implemented by a processor such as processor 34 that is executing programmed instructions stored as programs 50. Alternatively, some of the steps of the methods may be implemented in hardware such as control circuitry 41. In many cases, steps may be re-ordered, and some steps may be eliminated. It will be further understood that this disclosure is not limited to implantable devices. Any medical device that classifies postures for use in delivering therapy may utilize techniques of the current disclosure. Thus, the description of the embodiments discussed above are merely exemplary, with the scope of the invention to be defined by the Claims that follow.

What is claimed is:

1. A method, comprising:
    obtaining a detected parameter value for use in classifying a posture state of a patient;
    for each of multiple posture state definitions, obtaining a respective defined parameter value and a respective therapy parameter value;
    determining, for each of a plurality of the posture state definitions, a similarity between the detected parameter value and the respective defined parameter value;
    determining a blended therapy parameter value based on the similarities and respective therapy parameter values for the plurality of the posture state definitions; and
    delivering therapy to the patient via a medical device according to the blended therapy parameter value.

2. The method of claim 1, wherein the detected parameter value is indicative of a posture of the patient, each of the defined parameter values is indicative of a respective defined posture, and wherein determining, for each of a plurality of the posture state definitions, a similarity comprises determining, for each of the plurality of the posture state definitions, how close the posture of the patient is to the defined posture that is indicated by the respective defined parameter value.

3. The method of claim 2, wherein the detected parameter value comprises a detected posture vector, wherein the respective defined parameter value comprises a respective defined posture vector, and wherein determining, for each of a plurality of the posture state definitions, a similarity further comprises determining, for each of the plurality of the posture state definitions, a cosine of an angle between the detected posture vector and the respective defined posture vector.

4. The method of claim 1, wherein determining, for each of a plurality of the posture state definitions, a similarity between the detected parameter value and the respective defined parameter value comprises selecting the plurality of the posture state definitions.

5. The method of claim 1, further comprising determining a respective weighting factor W for each of the similarities and wherein determining a blended therapy parameter value comprises using the respective weighting factor to weight a respective therapy parameter value.

6. The method of claim 5, wherein each weighting factor is determined using a weighting function.

7. The method of claim 6, wherein determining, for each of a plurality of the posture state definitions, a similarity between the detected parameter value and the respective defined parameter value comprises determining a distance between the detected parameter value and the respective defined parameter value, and further comprising selecting the weighting function to map the distance to a value between 0 and a predetermined maximum positive number.

8. The method of claim 5, wherein each of the plurality of posture state definitions is included in a set I and the respective therapy parameter value is a therapy parameter value P, and wherein the blended therapy parameter value is determined as $$\frac{\sum_{i \in I} W_i \cdot P_i}{\sum_{i \in I} W_i}.$$

9. The method of claim 1, further comprising selecting a subset of multiple positive ones of the similarities for use in determining the blended therapy parameter value.

10. The method of claim 1, further comprising:
    determining a weighting factor for each of the similarities;
    normalizing each of the weighting factors; and
    classifying the posture state based on the normalized weighting factors.

11. The method of claim 1, further comprising:
    using selected ones of the similarities to determine time-averaged weighting factors;
    normalizing all of the time-averaged weighting factors with respect to each other; and
    determining from any one of the normalized time-averaged weighting factors an amount of time attributable to an associated one of the multiple posture state definitions over a predetermined period of time.

12. The method of claim 1, wherein the detected parameter value is indicative of a posture of the patient, and further comprising:
    obtaining a second detected parameter value for use in classifying an activity state of a patient;
    determining, for each of a second plurality of the posture state definitions, a similarity between the second detected parameter value and the respective defined parameter value;
    using the similarity between the second detected parameter value and the respective defined parameter value to weight the respective therapy parameter value;
    determining a second blended therapy parameter value based the weighted therapy parameter values; and
    delivering therapy to the patient according to the blended therapy parameter value and the second blended therapy parameter value.

13. The method of claim 1, further comprising delivering electrical stimulation therapy to the patient by an implantable medical device according to the blended therapy parameter value.

14. The method of claim 1, wherein the detected parameter value is indicative of motion of the patient, and wherein the blended therapy parameter value is adapted to deliver therapy to the patient in response to the motion.

15. A system, comprising:
 a sensor configured to provide a detected parameter value indicative of a posture state of a patient;
 a storage device configured to store posture state definitions, each posture state definition being associated with a defined parameter value and a therapy parameter value; and
 a processor configured to perform the steps of:
  determining a similarity between the detected parameter value and each of a plurality of the defined parameter values associated with a plurality of the posture state definitions; and
  determining a blended therapy parameter value for use in delivering therapy to the patient based on the similarities and on the therapy parameter values associated with the plurality of the posture state definitions.

16. The system of claim 15, wherein the detected parameter value indicates a detected posture vector, the defined parameter values each indicates a defined posture vector, and wherein the processor is further configured to determine the similarity based on how close the detected posture vector is to a defined posture vector.

17. The system of claim 16, wherein the processor is further configured to determine the similarity based on a cosine of an angle between the detected posture vector and a defined posture vector.

18. The system of claim 15, wherein the processor is further configured to perform the steps of:
 determining a respective weighting factor from each similarity;
 multiplying each weighting factor by a therapy parameter value for an associated posture state definition to obtain a weighted therapy parameter value;
 obtaining a sum of all of the weighted therapy parameter values; and
 determining the blended therapy parameter value by dividing the obtained sum by a sum of all of the weighting factors.

19. The system of claim 15, further comprising a therapy module configured to deliver therapy to the patient based on the blended therapy parameter value.

20. The system of claim 15, wherein the storage device is configured to store weighting functions and wherein the processor is further configured to perform the steps of:
 selecting one of the weighting functions;
 employing the selected weighting function to determine for each of selected ones of the similarities a respective weighting factor; and
 determining the blended therapy parameter value based on the weighting factors.

21. The system of claim 15, wherein the processor is further configured to perform the steps of:
 determining for a similarity a respective weighting factor;
 time-averaging the weighting factor; and
 employing the time-averaged weighting factor to obtain an amount of time attributable to an associated defined posture state.

22. The system of claim 15, wherein the posture state definitions include at least one of activity state definitions and posture definitions.

23. A non-transitory storage medium storing executable instructions to cause a processing circuit to perform the steps, comprising:
 receiving a detected parameter value indicative of a posture of a patient;
 obtaining multiple posture definitions describing defined postures;
 obtaining, for each of the multiple posture definitions, a respective therapy parameter value;
 determining multiple similarities, each describing how similar the detected parameter value is to a defined parameter value of a respective posture definition;
 obtaining for each of the posture definitions a weighted therapy parameter value that is based on the similarity determined for the posture definition and the respective therapy parameter value obtained for the posture definition; and
 obtaining a blended therapy parameter value based on the weighted therapy parameter values.

24. The non-transitory storage medium of claim 23, wherein the steps further comprise controlling delivery of therapy according to at least one of the blended therapy parameter value and a therapy parameter value obtained for a respective one of the postures definitions.

25. The non-transitory storage medium of claim 23, wherein the steps further comprise:
 receiving a detected parameter value indicative of an activity level of a patient; and
 modifying the blended therapy parameter value to take into account the activity level of the patient.

26. The non-transitory storage medium of claim 23, wherein the steps further comprise:
 classifying the posture of the patient based on the posture definitions; and
 controlling delivery of therapy to the patient based on the blended therapy parameter value if the patient is not classified as being in any of the defined postures, and otherwise, controlling delivery of therapy to the patient based on a therapy parameter value obtained for a posture definition describing the posture in which the patient is classified.

27. The non-transitory storage medium of claim 23, wherein the steps further comprise:
 selecting a weighting function;
 using the weighting function to determine a respective weighting factor for each of the similarities; and
 for each of the posture definitions, obtaining a weighted therapy parameter value for the posture definition by multiplying the respective weighting factor by the respective therapy parameter value obtained for the posture definition.

28. A method, comprising:
 obtaining from a sensor carried by a patient a signal indicative of a posture of the patient;
 comparing the signal to each of multiple posture definitions to obtain multiple similarities, each describing how similar the posture is to a respective posture definition;
 providing a classification of the posture that is based on the multiple similarities; and
 providing care to the patient via a medical device based on the classification.

29. The method of claim 28, wherein providing care to the patient comprises providing therapy to the patient via an implantable medical device based on the classification.

30. The method of claim 28, further comprising storing the classification for analyzing a condition of the patient.

31. The method of claim 28, wherein the classification of the postures is based on an array of values, each of the values being derived from a respective one of the multiple similarities and describing a portion of the posture attributable to a respective posture definition.

32. The method of claim 28, wherein providing care to the patient comprises providing neurostimulation therapy to the patient via an implantable medical device based on the classification.

* * * * *